(12) United States Patent
Ravikumar et al.

(10) Patent No.: US 6,610,842 B1
(45) Date of Patent: Aug. 26, 2003

(54) PROCESSES FOR THE SYNTHESIS OF OLIGOMERS USING PHOSPHORAMIDITE COMPOSITIONS

(75) Inventors: Vasulinga T. Ravikumar, Carlsbad, CA (US); Daniel C. Capaldi, Encinitas, CA (US); Douglas L. Cole, San Diego, CA (US)

(73) Assignee: ISIS Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 09/306,278

(22) Filed: May 6, 1999

(51) Int. Cl.$^7$ ............................ C07H 21/00; C07H 21/02
(52) U.S. Cl. ............................... 536/25.34; 536/25.31; 536/25.33; 536/25.14; 536/23.1; 536/22.1; 536/25.3
(58) Field of Search ........................... 536/25.34, 23.1, 536/22.1, 25.3, 25.31, 25.33, 25.14

(56) References Cited

U.S. PATENT DOCUMENTS

| | | | |
|---|---|---|---|
| 3,687,808 A | 8/1972 | Merigan et al. | 195/28 |
| 4,415,732 A | 11/1983 | Caruthers et al. | 536/27 |
| 4,458,066 A | 7/1984 | Caruthers et al. | 536/27 |
| 4,500,707 A | 2/1985 | Caruthers et al. | 536/27 |
| 4,668,777 A | 5/1987 | Caruthers et al. | 536/27 |
| 4,725,677 A | 2/1988 | Köster et al. | 536/27 |
| 4,816,571 A | 3/1989 | Andrus et al. | 536/27 |
| 4,973,679 A | 11/1990 | Caruthers et al. | 536/27 |
| 5,026,838 A | 6/1991 | Nojiri et al. | 536/27 |
| 5,132,418 A | 7/1992 | Caruthers et al. | 536/27 |
| RE34,069 E | 9/1992 | Köster et al. | 536/27 |
| 5,153,319 A | 10/1992 | Caruthers et al. | 536/27 |
| 5,204,455 A | 4/1993 | Froehler et al. | 536/22.1 |
| 5,212,295 A | 5/1993 | Cook | 536/26.7 |
| 5,453,496 A | 9/1995 | Caruthers et al. | 536/24.5 |
| 5,614,621 A | 3/1997 | Ravikumar et al. | 536/25.34 |
| 5,670,633 A | 9/1997 | Cook et al. | 536/23.1 |
| 5,705,621 A | 1/1998 | Ravikumar | 536/23.1 |
| 5,760,209 A | 6/1998 | Cheruvallath et al. | 536/25.34 |
| 5,783,690 A | * 7/1998 | Cheruvallath et al. | 536/55.3 |
| 5,808,035 A | 9/1998 | Usher et al. | 536/23.1 |
| 6,069,243 A | 5/2000 | Scozzari | 536/25.34 |

FOREIGN PATENT DOCUMENTS

EP  0 506 242 A1  3/1992

OTHER PUBLICATIONS

Marshall, W.S. et al., "Oligonucleotide synthesis as a tool in drug discovery research", *Drug Discovery Today*, 1998, 3(1), 34–42.

Agrawal et al. (eds.), "Methods of Molecular Biology", in *Protocols for Oligonucleotide Conjugates*, Agrawal, S. (ed.), Humana Press, New Jersey, 1994, vol. 26, 1–72.

Alul, R.H. et al., "Oxalyl–CPG: a labile support for synthesis of sensitive oligonucleotide derivatives", *Nucl. Acid Res.*, 1991, 19, 1527–1532.

Beaucage, S.L. et al., "Advances in the Synthesis of Oligonucleotides by the Phosphoramidite Approach", *Tetrahedron*, 1992, 48, 2223–2311.

Beaucage, S.L. et al., "The Synthesis of Specific Ribonucleotides and Unrelated Phosphorylated Biomolecules by the Phosphoramidite Method," *Tetrahedron*, 1993, 49(46), 10441–10488.

Beaucage, S.L. et al., "The Functionalization of Oligonucleotides Via Phosphoramidite Derivatives," *Tetrahedron*, 1993, 49(10), 1925–1963.

Bielinska, A. et al., "Regulation of Gene Expression with Double–Stranded Phosphorothioate Oligonucleotides", *Science*, 1990, 250, 997–1000.

Brown, T. et al., "Modern machine–aided methods of oligodeoxyribonucleotide synthesis", *Oligonucleotides and Analogs A Practical Approach*, 1991, Chapter 1, Ekstein, F., ed., IRL Press, Oxford, 1–24.

Cook, P.D., "Medicinal Chemistry of Antisense Oligonucleotides—future opportunities", *Anti–Cancer Drug Design*, 1991, 6, 585–607.

Crooke, S.T. et al., "Pharmacokinetic Properties of Several Novel Oligonucleotide Analogs in mice", *J. Pharmacol. Exp. Therapeutics*, 1996, 277, 923–937.

Delgado, C. et al., "The Uses and Properties of PEG–Linked Proteins", *Crit. Rev. in Therapeutic Drug Carrier Sys.*, 1992, 9, 249–304.

Efimov, V.A. et al., "New efficient sulfurizing reagents for the preparation of oligodeoxyribonucleotide phosphorothioate analogues", *Nucl. Acids Res.*, 1995, 23, 4029–4033.

Englisch, U. et al., "Chemically Modified Oligonucleotides as Probes and Inhibitors", *Angew. Chem. Int. Ed. Eng.*, 1991, 30, 613–629.

Hamm, M. L. et al., "Incorporation of 2'–Deoxy–2'–mercaptocytidine into Oligonucleotides via Phosphoramidite Chemistry," *J. Org. Chem.*, 1997, 62, 3415–3420.

Iyer, R.P. et al., "The Automated Synthesis of Sulfur–Containing Oligodeoxyribonucleotides Using 3H–1, 2–Benzodithiol–3–one 1,1–Dioxide as a Sulfur–Transfer Reagent", *J. Org. Chem.*, 1990, 55, 4693–4699.

Iyer, R.P. et al., "3H–1,2–Benzodithiole–3–one 1,1–Dioxide as an Improved Sulfurizing Reagent in the Solid–Phase Synthesis of Oligodeoxyribonucleoside Phosphorothioates", *J. Am. Chem. Soc.*, 1990, 112, 1253–1254.

(List continued on next page.)

Primary Examiner—James O. Wilson
Assistant Examiner—Howard V. Owens, Jr.
(74) Attorney, Agent, or Firm—Woodcock Washburn LLP

(57) ABSTRACT

Synthetic processes are provided wherein oligomers are prepared using phosphoramidite compositions. Oligomers having phosphodiester, phosphorothioate, phosphorodithioate covalent linkages are prepared that can include other covalent linkages. Also provided are compositions useful in such processes.

54 Claims, No Drawings

OTHER PUBLICATIONS

Kabanov, A.V.,"A new class of antivirals: antisense olgonucleotides combined with a hydrophobic substituent effectively inhibit influenza virus reproduction and synthesis of virus–specific proteins in MDCK cells", *FEBS Letts.*, 1990, 259, 327–330.

Kamer, P.C.J. et al., "An Efficient Approach Toward the Synthesis of Phosphorothioate Diesters via the Schonberg Reaction", *Tetrahedron Letts.*, 1989, 30, 6757–6760.

Kroschwitz, J.I., "Polynucleotides", *Concise Encyclopedia of Polymer Science and Engineering,* 1990, John Wiley & Sons, New York, 858–859.

Letsinger, R.L. et al., "Cholesteryl–conjugated oligonucleotides: Synthesis, properties and activity as inhibitors of replication of human immunodeficiency virus in cell culture", *Proc. Natl. Acad. Sci.,* 1989, 86, 6553–6556.

Manoharan, M. et al., "Lipidic Nucleic Acids", *Tetrahedron Letts.,* 1995, 36, 3651–3654.

Manoharan M. et al., "Cholic Acid–Oligonucliotide Conjugates for Antisense Applications", *Bioorganic Med. Chem. Letts.,* 1994, 4, 1053–1060.

Manoharan, M. et al., "Chemical Modifications to Improve Uptake and Bioavailability of Antisense Oligonucleotides", *Annals NY Acad. Sciences,* 1992, 660, 306–309.

Manoharan, M. et al., "Introduction of a Lipophilic Thioether Tether in the Minor Groove of Nucleic Acids for Antisense Applications", *Bioorg. Med. Chem. Letts.,* 1993, 3, 2765–2770.

Manoharan M. et al., "Oligonucleotide Conjugates: Alteration of the Pharmacokinetic Properties of Antisense Agents", *Nucleosides and Nucleotides,* 1995, 14, 969–973.

Mishra, R.K. et al., "Improved leishmanicidal effect of phosphorotioate antisense oligonucleotides by LDL–medicated delivery", *Biochim. Et Biophysica,* 1995, 1264, 229–237.

Oberhauser, B. et al., "Effective incorporation of 2'–O–methyl–oligonucleotides into liposomes and enhanced cell association through modification with thiocholesterol", *Nucl. Acids Res.,* 1992, 20, 533–538.

Ouchi, T. et al., "Synthesis and Antitumor Activity of Poly(Ethylene Glycol)s Linked to 5'–Fluorouracil via a Urethane or Urea Bond", *Drug Des. & Disc.,* 1992, 9, 93–105.

Polushin, N. N. et al., "Synthesis of Oligonucleotides Containing 2'–Azido–and 2'–Amino–2'–deoxyuridine Using Phosphotriester Chemistry," *Tetrahedron Letts.,* 1996, 37(19), 3227–3230.

Rao, M.V. et al., "Dibenzoyl Tetrasulphide–A Rapid Sulphur Transfer Agent in the Synthesis of Phosphorothioate Analogues of Oligonucleotides", *Tetrahedron Letts.,* 1992, 33, 4839–4842.

Ravasio, N. et al., "Selective Hydrogenations Promoted by Copper Catalysts. 1. Chemoselectivity, Regioselectivity, and Stereoselectivity in the Hydrogenation of 3–Substituted Steroids", *J. Org. Chem.,* 1991, 56, 4329–4333.

Saison–Behmoaras, T. et al., "Short modified antisense oligonucleotides directed against Ha–ras point mutation induce selective cleavage of the mRNA and inhibit T24 cells proliferation", *EMBO J.,* 1991, 10, 1111–1118.

Sanghvi, Y.S., "Heterocyclic Base Modifications in Nucleic acids and their Applications in Antisense Oligonucleotides", *Antisense Research and Applications,* 1993, Chapter 15, CRC Press, Boca Raton, 273–288.

Secrist, J.A. et al., "Synthesis and Biological Activity of 4'–Thionucleosides", *10th International Roundtable: Nucleosides, Nucleotides and their Biological Applications,* Sep. 16–20, 1992, Abstract 21, Park City, Utah, 40.

Shea, R.G. et al., "Synthesis, hybridization properties and antiviral activity of lipid–oligodeoxynucletide conjugates", *Nucl. Acids Res.,* 1990, 18, 3777–3783.

Stec, W.J. et al., "Bis (O,O–Diisopropoxy Phosphinothioyl) Disulfide—A Highly Efficient Sulfurizing Reagent for Cost-Effective Synthesis of Oligo(Nucleoside Phosphorothioate)s", *Tetrahedron Letts.,* 1993, 34, 5317–5320.

Stec, W.J. et al., "Novel route to oligo(deoxyribonucleoside phosphorothioates). Stereocontrolled synthesis of P–chiral oligo(deoxyribonucleoside phosphorothioates)", *Nucl. Acids Res.,* 1991, 19, 5883–5888.

Stec, W.J. et al., "Stereospecific Synthesis of P–chiral Analogs of oligonucleotides", *Methods in Molecular Biology,* 1993, vol. 20, Chapter 14, Humana Press, Totowa, NJ, 285–313.

Svinarchuk, F.P. et al., "Inhibition of HIV proliferation in MT–4 cells by antisense oligonucleotide conjugated to lipophilic groups", *Biochimie,* 1993, 79, 49–54.

Thomson, J. B. et al., "Synthesis and Properties of Diuridine Phosphate Analogues Containing Thio and Amino Modifications," *J. Org. Chem.,* 1996, 61, 6273–6281.

Vu, H. et al, "Internucleotide Phosphite Sulfurization with Tetraethylthiuram Disulfide. Phosphorothioate Oligonucleotide Synthesis via Phosphoramidite Chemistry", *Tetrahedron Letts.,* 1991, 32, 3005–3008.

Wright, P. et al., "Large Scale Synthesis of Oligonucleotides via phosphoramidite Nucleosides and a High–loaded Polystyrene Support", *Tetra. Letts.,* 1993, 34, 3373–3376.

Wu, H. et al., "Inhibition of in vitro transcription by specific double–stranded oligodeoxyribonucleotides", *Gene,* 1990, 89, 203–209.

Xu, Q. et al., "Use of 1,2,4–dithiazolidine (DtsNH) and 3–ethoxy–1,2,4–dithiazoline–5–one (EDITH) for synthesis of phosphorothioate–containing oligodeoxyribonucleotides", *Nucl. Acids Res.,* 1996, 24, 1602–1607.

Xu, Q. et al., "Efficient introduction of phosphorothioates into RNA oligonucleotides by 3–ethoxy–1,2, 4–dithiazoline–5–one (EDITH)", *Nucl. Acids Res.,* 1996, 24, 3643–3644.

Agrawal, S. (ed.), *Protocols for Oligonucleotides and Analogs,* Humana Press, Totowa, NJ, 1993.

Ausubel, F.M. et al. (eds.), *Current Protocols in Molecular Biology,* Current Publications, 1993.

Eckstein (ed.), *Oligonucleotides and Analogues, A Practical Approach,* IRL Preess, New York, 1991.

Green and Wuts, *Protective Groups in Organic Synthesis,* 2d Ed., John Wiley & Sons, New York, Chapter 2, 1991.

Gait (ed.), *Oligonucleotide Synthesis, A Practical Approach,* IRL Press, New York, 1984.

Sambrook, J. et al. (eds.), *Molecular Cloning, A Laboratory Manual,* Second Ed., Cold Spring Harbor Laboratory Press, 1989.

\* cited by examiner

SEQUENCE LISTING

```
<160> NUMBER OF SEQ ID NOS: 5

<210> SEQ ID NO 1
<211> LENGTH: 20
<212> TYPE: DNA
<213> ORGANISM: Artificial Sequence
<220> FEATURE:
<223> OTHER INFORMATION: Novel Sequence

<400> SEQUENCE: 1
tcccgcctgt gacatgcatt                                               20

<210> SEQ ID NO 2
<211> LENGTH: 20
<212> TYPE: DNA
<213> ORGANISM: Artificial Sequence
<220> FEATURE:
<223> OTHER INFORMATION: Novel Sequence

<400> SEQUENCE: 2
gcccaagctg gcatccgtca                                               20

<210> SEQ ID NO 3
<211> LENGTH: 21
<212> TYPE: DNA
<213> ORGANISM: Artificial Sequence
<220> FEATURE:
<223> OTHER INFORMATION: Novel Sequence

<400> SEQUENCE: 3
gcgtttgctc ttcttcttgc g                                             21

<210> SEQ ID NO 4
<211> LENGTH: 20
<212> TYPE: DNA
<213> ORGANISM: Artificial Sequence
<220> FEATURE:
<223> OTHER INFORMATION: Novel Sequence

<400> SEQUENCE: 4
```

```
gttctcgctg gtgagtttca                    20
```

<210> SEQ ID NO 5
<211> LENGTH: 20
<212> TYPE: DNA
<213> ORGANISM: Artificial Sequence
<220> FEATURE:
<223> OTHER INFORMATION: Novel Sequence

<400> SEQUENCE: 5

```
tccgtcatcg ctcctcaggg                    20
```

PROCESSES FOR THE SYNTHESIS OF OLIGOMERS USING PHOSPHORAMIDITE COMPOSITIONS

FIELD OF THE INVENTION

The present invention is directed to methods of using phosphoramidite compositions for the preparation of oligomers having phosphite, phosphodiester, phosphorothioate, or phosphorodithioate.

BACKGROUND OF THE INVENTION

Oligonucleotides and their analogs have been developed and used in molecular biology in a variety of procedures as probes, primers, linkers, adapters, and gene fragments. Modifications to oligonucleotides used in these procedures include labeling with nonisotopic labels, e.g. fluorescein, biotin, digoxigenin, alkaline phosphatase, or other reporter molecules. Other modifications have been made to the ribose phosphate backbone to increase the nuclease stability of the resulting analog. Examples of such modifications include incorporation of methyl phosphonate, phosphorothioate, or phosphorodithioate linkages, and 2'-O-methyl ribose sugar units. Further modifications include those made to modulate uptake and cellular distribution. With the success of these compounds for both diagnostic and therapeutic uses, there exists an ongoing demand for improved oligonucleotides and their analogs.

It is well known that most of the bodily states in multicellular organisms, including most disease states, are effected by proteins. Such proteins, either acting directly or through their enzymatic or other functions, contribute in major proportion to many diseases and regulatory functions in animals and man. For disease states, classical therapeutics has generally focused upon interactions with such proteins in efforts to moderate their disease-causing or disease-potentiating functions. In newer therapeutic approaches, modulation of the actual production of such proteins is desired. By interfering with the production of proteins, the maximum therapeutic effect may be obtained with minimal side effects. It is therefore a general object of such therapeutic approaches to interfere with or otherwise modulate gene expression, which would lead to undesired protein formation.

One method for inhibiting specific gene expression is with the use of oligonucleotides, especially oligonucleotides which are complementary to a specific target messenger RNA (mRNA) sequence. Several oligonucleotides are currently undergoing clinical trials for such use. Phosphorothioate oligonucleotides are presently being used as such antisense agents in human clinical trials for various disease states, including use as antiviral agents.

Transcription factors interact with double-stranded DNA during regulation of transcription. Oligonucleotides can serve as competitive inhibitors of transcription factors to modulate their action. Several recent reports describe such interactions (see Bielinska, A., et. al., *Science*, 1990, 250, 997–1000; and Wu, H., et. al., *Gene*, 1990, 89, 203–209).

In addition to such use as both indirect and direct regulators of proteins, oligonucleotides and their analogs also have found use in diagnostic tests. Such diagnostic tests can be performed using biological fluids, tissues, intact cells or isolated cellular components. As with gene expression inhibition, diagnostic applications utilize the ability of oligonucleotides and their analogs to hybridize with a complementary strand of nucleic acid. Hybridization is the sequence specific hydrogen bonding of oligomeric compounds via Watson-Crick and/or Hoogsteen base pairs to RNA or DNA. The bases of such base pairs are said to be complementary to one another.

Oligonucleotides and their analogs are also widely used as research reagents. They are useful for understanding the function of many other biological molecules as well as in the preparation of other biological molecules. For example, the use of oligonucleotides and their analogs as primers in PCR reactions has given rise to an expanding commercial industry. PCR has become a mainstay of commercial and research laboratories, and applications of PCR have multiplied. For example, PCR technology now finds use in the fields of forensics, paleontology, evolutionary studies and genetic counseling. Commercialization has led to the development of kits which assist non-molecular biology-trained personnel in applying PCR. Oligonucleotides and their analogs, both natural and synthetic, are employed as primers in such PCR technology.

Oligonucleotides and their analogs are also used in other laboratory procedures. Several of these uses are described in common laboratory manuals such as *Molecular Cloning, A Laboratory Manual*, Second Ed., J. Sambrook, et al., Eds., Cold Spring Harbor Laboratory Press, 1989; and *Current Protocols In Molecular Biology*, F. M. Ausubel, et al., Eds., Current Publications, 1993. Such uses include as synthetic oligonucleotide probes, in screening expression libraries with antibodies and oligomeric compounds, DNA sequencing, in vitro amplification of DNA by the polymerase chain reaction, and in site-directed mutagenesis of cloned DNA. See Book 2 of *Molecular Cloning, A Laboratory Manual*, supra. See also "DNA-protein interactions and The Polymerase Chain Reaction" in Vol. 2 of *Current Protocols In Molecular Biology*, supra.

Oligonucleotides and their analogs can be synthesized to have customized properties that can be tailored for desired uses. Thus a number of chemical modifications have been introduced into oligomers to increase their usefulness in diagnostics, as research reagents and as therapeutic entities. Such modifications include those designed to increase binding to a target strand (i.e. increase their melting temperatures, Tm), to assist in identification of the oligonucleotide or an oligonucleotide-target complex, to increase cell penetration, to stabilize against nucleases and other enzymes that degrade or interfere with the structure or activity of the oligonucleotides and their analogs, to provide a mode of disruption (terminating event) once sequence-specifically bound to a target, and to improve the pharmacokinetic properties of the oligonucleotide.

The chemical literature discloses numerous well-known protocols for coupling nucleosides through phosphorous-containing covalent linkages to produce oligonucleotides of defined sequence. One of the most routinely used protocols is the phosphoramidite protocol (see, e.g., Advances in the Synthesis of Oligonucleotides by the Phosphoramidite Approach, Beaucage, S. L.; Iyer, R. P., *Tetrahedron*, 1992, 48, 2223–2311 and references cited therein), wherein a nucleoside or oligonucleotide having a free hydroxyl group is reacted with a protected cyanoethyl phosphoramidite monomer in the presence of a weak acid to form a phosphite-linked structure. Oxidation of the phosphite linkage followed by hydrolysis of the cyanoethyl group yields the desired phosphodiester or phosphorothioate linkage.

Phosphoramidites are commercially available from a variety of commercial sources (included are: Glen Research, Sterling, Va.; Amersham Pharmacia Biotech Inc., Piscataway, N.J.; Cruachem Inc., Aston, Pa.; Chemgenes Corporation, Waltham, Mass.; Proligo LLC, Boulder, Colo.; PE Biosystems, Foster City Calif.; Beckman Coulter Inc., Fullerton, Calif.). Purity of commercially available phosphoramidites are generally around 98 or 99%. Some commercial sources set a standard and claim that all phosphoramidites are equal to or higher purity than the set standard. Alternatively, some commercial sources include assay results for each batch of phosphoramidites sent out. Commercially available phosphoramidites are prepared for the most part for automated DNA synthesis and as such are prepared for immediate use for synthesizing desired sequences of oligonucleotides. The high purity has been taught in the art to be a requisite to adequate coupling efficiency during synthesis.

A representative example of the rigorous quality assurance criteria applied to commercially available phosphoramidites is illustrated in the Glen Research Catalog. After synthesis and purification each phosphoramidite is subjected to quality assurance tests. Included in these tests is HPLC purification which results are used to establish the identity and purity of the particular amidite. Further tests include TLC, $^{31}P$ NMR, a coupling test, a solution test, and a loss on drying test. The threshold purity of these amidites from this supplier is set at greater than 98%. The manufacturer further determines by $^{31}P$ NMR that aside from the phosphoramidite no other phosphorus species are present.

Oligonucleotide synthesis has evolved as a practice that has been reported to required an almost antiseptic environment to obtain the desired product or a reasonable amount of product having a reasonable purity. This dogma has been stressed in a number of books dedicated to the synthesis of oligonucleotides and analogs. In Oligonucleotides and Analogues, A Practical Approach, Eckstein Ed, IRL Press; New York, 1991; the coupling efficiency e.g. average stepwise yield, is stated to be the primary factor in the over yield and purity of a product oligonucleotide. For example it is shown that a coupling efficiency of 99.5% will give a 90.9% overall yield for the synthesis of a 20-mer. If the coupling efficiency is reduced to only 90% the overall yield of the 20-mer drops to 13.5%. Hence, it can be seen that the coupling efficiency is very controlling, especially for oligonucleotides greater than about a 10-mer (38.7% overall yield with a 90% coupling efficiency). It is further stated that a coupling efficiency of less than 98% is totally unacceptable for routine oligonucleotide synthesis of longer sequences. Another factor that results directly from a low yield is that purification of the final oligonucleotide becomes much more difficult and costly. To achieve a good average coupling efficiency the use of good quality reagents is stressed.

Oligonucleotide Synthesis, a Practical Approach, Gait Ed, IRL Press; New York, 1984; is another publication detailing the synthesis of oligonucleotides. It also stresses the importance of using "the highest purity of batches of reagents". The effect of impurities at each coupling is stated to be accumulative requiring removal from the final oligonucleotide after synthesis. It is further stated that the purification of such impure oligonucleotides often require two separate purification procedures to give the desired purity.

The synthesis of oligonucleotides has classically involved obtaining a desired product which was in itself a challenge. The synthesis of oligonucleotides has more recently evolved to the point that routine syntheses are being performed on kilogram scale. Moving forward the next step is the synthesis of oligonucleotides and analogs on ton scale. The evolution of oligonucleotide synthetic techniques toward large scale is requiring a reevaluation of each aspect of the synthetic process. One such aspect is the cost of the phosphoramidites used in oligonucleotide synthesis.

Commercially available high purity phosphoramidites generally account for about 40% of the overall cost of oligonucleotide synthesis. This 40% reflects the synthesis of the phosphoramidite and the subsequent purification and analysis of the phosphoramidite prior to sale. A reduction in the cost of phosphoramidites could have a significant effect on the cost of oligonucleotides produced therefrom. Consequently, there remains a need in the art for synthetic methods that will overcome these problems.

Several processes are known for the solid phase synthesis of oligonucleotide compounds. These are generally disclosed in the following U.S. Pat. Nos. U.S. Pat. No. 4,458,066; issued Jul. 3, 1984; U.S. Pat. No. 4,500,707, issued Feb. 19, 1985; and U.S. Pat. No. 5,132,418, issued Jul. 21, 1992. Additionally, a process for the preparation of oligonucleotides using phosphoramidite intermediates is disclosed in U.S. Pat. No. 4,973,679, issued Nov. 27, 1990.

A process for the preparation of phosphoramidites is disclosed in U.S. Pat. No. 4,415,732, issued Nov. 15, 1983.

Phosphoramidite nucleoside compounds are disclosed in U.S. Pat. No. 4,668,777, issued May 26, 1987.

A process for the preparation of oligonucleotides using a β-eliminating phosphorus protecting group is disclosed in U.S. Pat. No. Re. 34,069, issued Sep. 15, 1992.

A process for the preparation of oligonucleotides using a β-eliminating or allylic phosphorus protecting group is disclosed in U.S. Pat. No. 5,026,838, issued Jun. 25, 1991.

SUMMARY OF THE INVENTION

The present invention discloses methods for the preparation of oligomers having at least one moiety of formula:

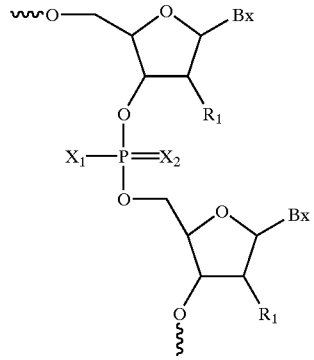

wherein:

each $X_1$ and $X_2$ is, independently, O or S;

Bx is a protected or unprotected heterocyclic base moiety; and $R_1$ is H, a protected hydroxyl group, a sugar substituent group or a protected sugar substituent group; comprising the steps of:

(a) providing a compound of the formula:

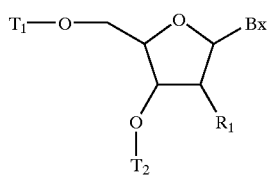

wherein:
T₁ is a hydroxyl protecting group; and
T₂ is a covalent attachment to a solid support or a solid support bound nucleoside, nucleotide, oligonucleoside or oligonucleotide;
(b) removing the T₁ group to form said compound having a 5'-hydroxyl group; and
(c) treating said compound having a 5'-hydroxyl group with a phosphoramidite composition to form an extended compound, said phosphoramidite composition comprising a phosphoramidite compound of the formula:

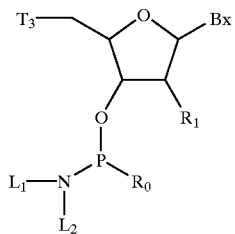

wherein:
T₃ is a protected hydroxyl group, a nucleoside, a nucleotide, an oligonucleoside or an oligonucleotide;
R₀ is a phosphorus protecting group; and
each L₁ and L₂ is, independently, $C_{1-6}$ alkyl;
or L₁ and L₂ are joined together to form a 4- to 7-membered heterocyclic ring system including the nitrogen atom to which said L₁ and L₂ are attached, wherein said ring system optionally includes at least one additional heteroatom selected from O, N, and S;
said phosphoramidite composition further comprising at least about 1% by weight of at least one 3'-hydroxy nucleoside, a $P^{III}$ species different from said phosphoramidite compound where covalent attachment of groups to the $P^{III}$ phosphorus of said $P^{III}$ species is through oxygen or sulfur, or a $P^V$ species where covalent attachment of groups to the $P^V$ species is through oxygen, sulfur or nitrogen.

In some preferred methods of the present invention, the phosphoramidite composition comprises at least about 2% by weight of at least one 3'-hydroxy nucleoside, a $P^{III}$ species different from said phosphoramidite compound where covalent attachment of groups to the $P^{III}$ phosphorus of said $P^{III}$ species is through oxygen or sulfur, or a $P^V$ species where covalent attachment of groups to the $P^V$ species is through oxygen, sulfur or nitrogen.

The methods of the present invention include treating the extended compound with a capping agent to form a capped compound which can be further treated with an oxidizing agent to form an oxidized compound. The methods also include treating the oxidized compound with a reagent effective to deprotect the oxidized compound to form a deprotected oligomer. The methods further include treating the deprotected oligomer with a reagent effective to cleave the deprotected oligomer from the solid support. The methods also include treating with a reagent effective to deprotect and cleave the oxidized compound simultaneously. The methods also include removing the 5'-hydroxyl group after the synthesis is complete.

Preferred heterocyclic base moieties include adenine, $N^6$-benzoyladenine, cytosine, $N^4$-benzoylcytosine, 5-methylcytosine, $N^4$-benzoyl-5-methylcytosine, thymine, uracil, guanine, $N^2$-isobutyrylguanine and 2-aminoadenine.

In one embodiment of the present invention each L₁ and L₂ is $C_{1-6}$ alkyl. In a preferred embodiment each L₁ and L₂ is isopropyl. In another embodiment L₁ and L₂ are joined together in a heterocyclic ring system which includes the nitrogen atom to which L₁ and L₂ are attached, the ring system optionally including at least one additional heteroatom selected from O, N and S. A preferred heterocyclic ring system is morpholine.

In one embodiment of the present invention each R₁, is, independently, H, hydroxyl, $C_1$–$C_{20}$ alkyl, $C_3$–$C_{20}$ alkenyl, $C_2$–$C_{20}$ alkynyl, halogen, thiol, keto, carboxyl, nitro, nitroso, nitrile, trifluoromethyl, trifluoromethoxy, O-alkyl, S-alkyl, NH-alkyl, N-dialkyl, O-aryl, S-aryl, NH-aryl, O-aralkyl, S-aralkyl, NH-aralkyl, amino, N-phthalimido, imidazole, azido, hydrazino, hydroxylamino, isocyanato, sulfoxide, sulfone, sulfide, disulfide, silyl, aryl, heterocycle, carbocycle, intercalator, reporter molecule, conjugate, polyamine, polyamide, polyalkylene glycol, or polyether;

or R, has formula I or II:

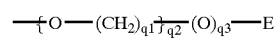  I

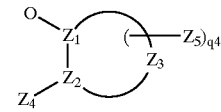  II wherein:
E is $C_1C_{10}$ alkyl, $N(Q_1)(Q_2)$ or $N=C(Q_1)(Q_2)$;
each Q₁ and Q₂ is, independently, H, $C_1$–$C_{10}$ alkyl, dialkylaminoalkyl, a nitrogen protecting group, a tethered or untethered conjugate group, a linker to a solid support;
or Q₁ and Q₂, together, form a nitrogen protecting group or a ring structure optionally including at least one additional heteroatom selected from N and O;
$q^1$ is an integer from 1 to 10;
$q^2$ is an integer from 1 to 10;
$q^3$ is 0 or 1;
$q^4$ is 0, 1 or 2;
Z₄ is $OM_1$, $SM_1$ or $N(M_1)_2$;
each M₁ is, independently, H, $C_1$–$C_8$ alkyl, $C_1$–$C_8$ haloalkyl, $C(=NH)N(H)M_2$, $C(=O)N(H)M_2$ or $OC(=O)N(H)M_2$;
M₂ is H or $C_1$–$C_8$ alkyl;
each Z₁, Z₂ and Z₃ is, independently, $C_4$–$C_7$ cycloalkyl, $C_5$–$C_{14}$ aryl or $C_3$–$C_{15}$ heterocyclyl; and
Z₅ is $C_1$–$C_{10}$ alkyl, $C_1$–$C_{10}$ haloalkyl, $C_2$–$C_{10}$ alkenyl, $C_2$–$C_{10}$ alkynyl, $C_6$–$C_{14}$ aryl, $N(Q_1)(Q_2)$, $OQ_1$, halo, $SQ_1$ or CN.

It is preferred that the heteroatom of said heterocyclyl group be selected from oxygen, nitrogen and sulfur. In one embodiment of the present invention the phosphorus protecting group is $X_3$—J, wherein $X_3$ is O or S. In a preferred embodiment J is $CH_2CH_2CN$, diphenylsilylethyl, δ-cyanobutenyl, cyano p-xylyl (CPX), methyl-N-trifluoroacetyl ethyl (META) or acetoxy phenoxy ethyl (APOE).

The methods of the present invention include compositions having at least one compound of one of the formulas shown below:

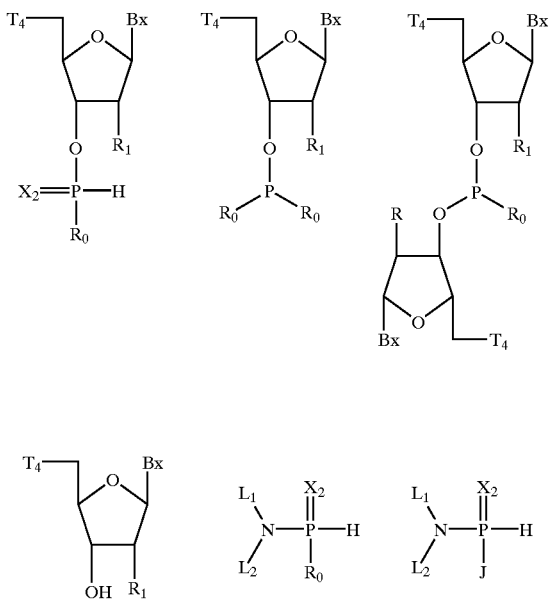

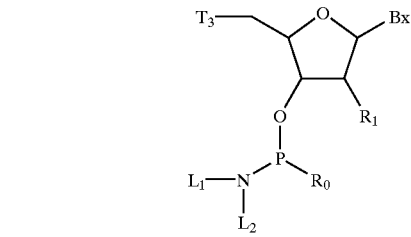

wherein:
  each $X_2$ is, independently, O or S;
  each J is $CH_2CH_2CN$, diphenylsilylethyl, δ-cyanobutenyl, cyano p-xylyl (CPX), methyl-N-trifluoroacetyl ethyl (META) or acetoxy phenoxy ethyl (APOE);
  each $T_4$ is, independently, a hydroxyl group or a protected hydroxyl group;
  each $R_0$ is a phosphorus protecting group,
  each $L_1$ and $L_2$ is, independently, $C_{1-6}$ alkyl;
  or $L_1$ and $L_2$ are joined together with the nitrogen atom to which they are attached to form a 4- to 7-membered heterocyclic ring system, wherein said ring system optionally includes at least one additional heteroatom selected from O, N and S;
  each Bx is a protected or unprotected heterocyclic base moiety; and
  each $R_1$ is, independently, H, a protected hydroxyl group, a sugar substituent group or a protected sugar substituent group.

In one embodiment of the present invention the phosphoramidite composition comprises at least about 98% by weight of the phosphoramidite compound. In another embodiment the phosphoramidite composition comprises at least about 97% by weight of the phosphoramidite compound. In yet another embodiment the phosphoramidite composition comprises at least about 95% by weight of the phosphoramidite compound. In another preferred embodiment the phosphoramidite composition comprises at least about 90% by weight of the phosphoramidite compound. In a more preferred embodiment the phosphoramidite composition comprises at least about 80% by weight of the phosphoramidite compound. In yet another preferred embodiment the phosphoramidite composition comprises at least about 75% by weight of the phosphoramidite compound.

In another embodiment of the present invention each $X_1$ and $X_2$ is, independently, O. In another embodiment each $X_1$ and $X_2$ is, independently, S. In a further embodiment one of said $X_1$ and $X_2$ is O and the other of said $X_1$ and $X_2$ is S.

In a preferred embodiment of the present invention the compound having a 5'hydroxyl group is treated with a phosphoramidite compound in the presence of an activating agent. In another preferred embodiment the activating agent is 1-H-tetrazole.

A further method of the present invention includes linking a nucleotide to a further nucleotide, nucleoside, oligonucleoside or oligonucleotide having a 5'-hydroxyl group thereon comprising treating the further nucleotide, nucleoside, oligonucleoside or oligonucleotide having a 5'-hydroxyl group with a phosphoramidite composition and an activating agent in a suitable solvent under conditions effective to form an extended compound, wherein said phosphoramidite composition is substantially enriched in a phosphoramidite compound of the formula:

wherein:
  $T_3$ is a protected hydroxyl group, a nucleoside, a nucleotide, an oligonucleoside or an oligonucleotide;
  $R_0$ is a phosphorus protecting group; and
  each $L_1$ and $L_2$ is, independently, $C_{1-6}$ alkyl;
  or $L_1$ and $L_2$ are joined together to form a 4- to 7-membered heterocyclic ring system including the nitrogen atom to which $L_1$ and $L_2$ are attached, wherein said ring system optionally includes at least one additional heteroatom selected from O, N and S;
  said phosphoramidite composition further comprising at least about 1% by weight of one or more impurities selected from 3'-hydroxy nucleoside, a $P^{III}$ species different from the phosphoramidite compound where covalent attachment of groups to the $P^{III}$ phosphorus of said $P^{III}$ species is through oxygen or sulfur, or a $P^V$ species where covalent attachment of groups to the $P^V$ species is through oxygen, sulfur or nitrogen. It is further preferred that said phosphoramidite composition comprise at least about 2% by weight of such impurities.

In another embodiment of the present invention oligomers are provided having a 2'–5' linkage. Said oligomers comprise a plurality of nucleosides wherein at least one nucleoside is connected to another nucleoside by a 2'–5' internucleoside linkage. Compositions having at least one 2'–5' linkage include at least one compound having one of the formulas:

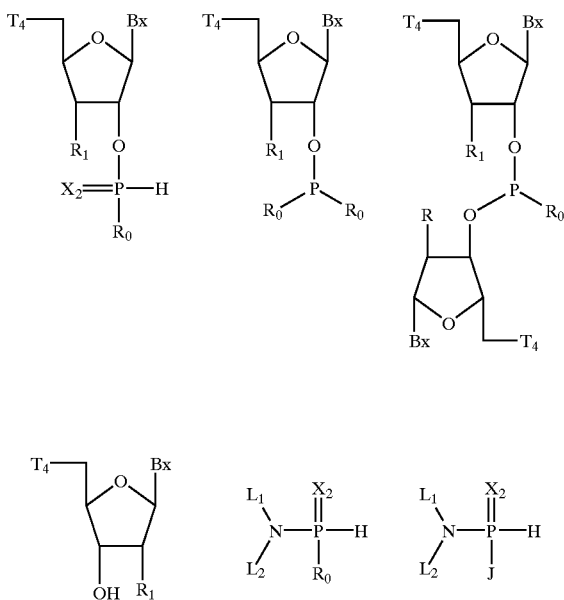

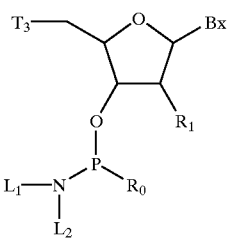

wherein the variables are as previously described.

The present invention also provides a phosphoramidite composition comprising at least one phosphoramidite compound of the formula:

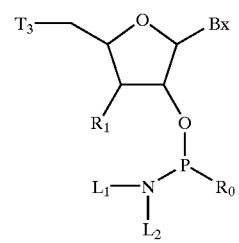

wherein:
  $T_3$ is a protected hydroxyl group, a nucleoside, a nucleotide, an oligonucleoside or an oligonucleotide;
  $R_0$ is a phosphorus protecting group; and
  each $L_1$ and $L_2$ 'is independently, $C_{1-6}$ alkyl;
  or $L_1$ and L2 are joined together to form a 4- to 7-membered heterocyclic ring system which includes the nitrogen atom to which $L_1$ and $L_2$ are attached, wherein said ring system optionally includes at least one additional heteroatom selected from O, N and S;
  said composition further comprising at least about 1% by weight of at least one 3'-hydroxy nucleoside, 2'-hydroxy nucleoside, $P^{III}$ species different from the phosphoramidite compound where covalent attachment of groups to the $P^{III}$ phosphorus of said $P^{III}$ species is through oxygen or sulfur, or a $P^V$ species where covalent attachment of groups to the $P^V$ species is through oxygen, sulfur or nitrogen.

It is further preferred that the phosphoramidite composition comprise at least about 2% by weight of at least one 3'-hydroxy nucleoside, 2'-hydroxy nucleoside, $P^{III}$ species different from the phosphoramidite compound where covalent attachment of groups to the $P^{III}$ phosphorus of said $P^{III}$ species is through oxygen or sulfur, or a $P^V$ species where covalent attachment of groups to the $P^V$ species is through oxygen, sulfur or nitrogen.

In one embodiment of the present invention the phosphoramidite composition comprises at least about 98% by weight of the phosphoramidite compound. In another embodiment the phosphoramidite composition comprises at least about 97% by weight of the phosphoramidite compound. In yet another embodiment the phosphoramidite composition comprises at least about 95% by weight of the phosphoramidite compound. In another preferred embodiment the phosphoramidite composition comprises at least about 90% by weight of the phosphoramidite compound. In a more preferred embodiment the phosphoramidite composition comprises at least about 80% by weight of the phosphoramidite compound. In yet another preferred embodiment the phosphoramidite composition comprises at least about 75% by weight of the phosphoramidite compound.

Included in the phosphoramidite composition is at least one compound having one of the formulas:

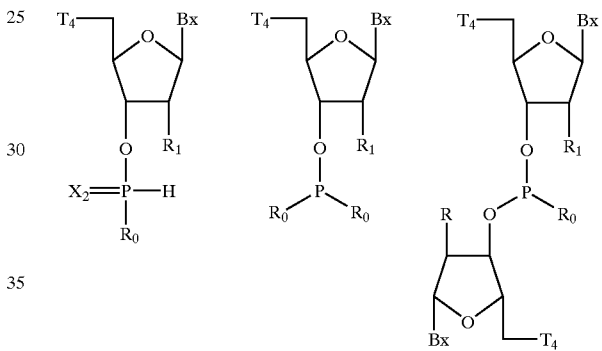

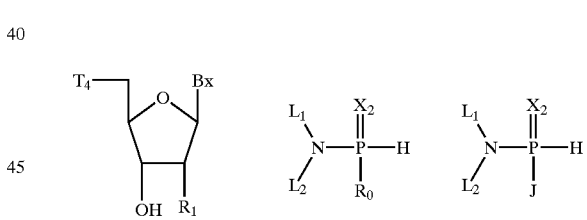

wherein the variables are as previously described above.

The present invention also provides a phosphoramidite composition having at least one phosphoramidite compound of the formula:

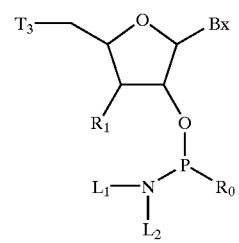

wherein the variables are as previously described above, the composition further including at least one compound having one of the formulas:

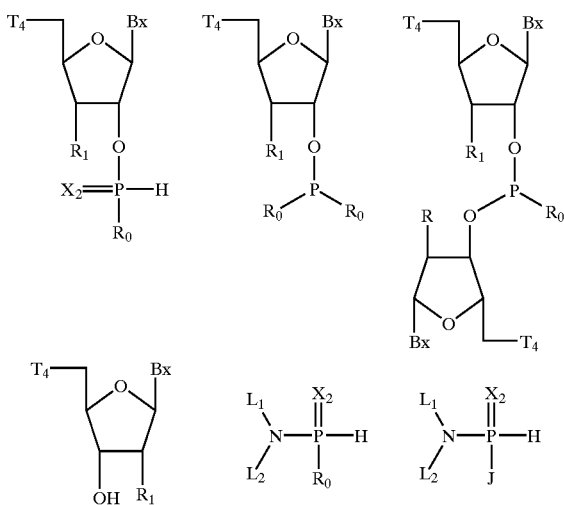

wherein the variables are as previously described above.

The present invention also presents a phosphoramidite composition comprising at least one phosphoramidite compound of the formula:

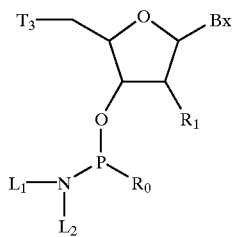

and at least about 1% by weight of at least one $P^{III}$ species different from said phosphoramidite compound where covalent attachment of groups to the $P^{III}$ phosphorus of said $P^{III}$ species is through oxygen or sulfur, or a $P^V$ species where covalent attachment of groups to the $P^V$ species is through oxygen, sulfur or nitrogen.

In another embodiment of the present invention the phosphoramidite composition comprises at least about 2% by weight of at least one $P^{III}$ species different from said phosphoramidite compound where covalent attachment of groups to the $P^{III}$ phosphorus of said $P^{III}$ species is through oxygen or sulfur, or a $P^V$ species where covalent attachment of groups to the $P^V$ species is through oxygen, sulfur or nitrogen.

DETAILED DESCRIPTION OF PREFERRED EMBODIMENTS

The present invention provides methods for the preparation of oligomers having phosphite, phosphodiester, phosphorothioate, or phosphorodithioate linkages. The present invention also provides compositions useful in the preparation of such oligomers. More particularly the methods are useful for the synthesis of oligomers utilizing phosphoramidite compositions as opposed to highly purified phosphoramidite compounds.

The present invention further provides methods for the preparation of oligomers using phosphoramidite protocols. In preferred embodiments the synthesis is performed using solid phase methods. Phosphoramidite compositions are substituted for highly purified phosphoramidite compounds that are traditionally used in oligonucleotide synthesis.

Phosphoramidite compositions as used in the present invention are substantially enriched with a phosphoramidite compound and contain further compounds which are essentially inert impurities. The phosphoramidite compositions of the present invention comprise at least about 1% by weight of such impurities. It is further preferred that the phosphoramidite compositions of the present invention comprise at least about 2% by weight of such impurities.

These impurities are side products resulting from the phosphoramidite synthesis. Different synthetic routes can lead to slightly different side products or impurities. Phosphoramidite compositions are prepared by synthesizing, precipitating and drying the product from a phosphoramidite synthesis without performing purification. Impurities or side products that can be present in the phosphoramidite composition of the present invention include a 3'-hydroxy nucleoside, a $P^{III}$ species different from said phosphoramidite compound where covalent attachment of groups to the $P^{III}$ phosphorus of said $P^{III}$ species is through oxygen or sulfur, a $P^V$ species where covalent attachment of groups to the $P^V$ species is through oxygen, sulfur or nitrogen, or other $P^{III}$ and $P^V$ phosphorus species.

The present invention utilizes phosphoramidite compositions wherein each composition is substantially enriched in a desired phosphoramidite compound and also contains at least one inert side product or impurity produced during the synthesis of the desired phosphoramidite compound. In one embodiment of the present invention the phosphoramidite composition comprises at least about 98% by weight of the phosphoramidite compound. In another embodiment the phosphoramidite composition comprises at least about 97% by weight of the phosphoramidite compound. In yet another embodiment the phosphoramidite composition comprises at least about 95% by weight of the phosphoramidite compound. In another preferred embodiment the phosphoramidite composition comprises at least about 90% by weight of the phosphoramidite compound. In a more preferred embodiment the phosphoramidite composition comprises at least about 80% by weight of the phosphoramidite compound. In yet another preferred embodiment the phosphoramidite composition comprises at least about 75% by weight of the phosphoramidite compound.

In one embodiment of the present invention phosphoramidite compositions are obtained by synthesizing the desired phosphoramidite compound using a standard method. Following synthesis the solvent is removed and the crude product is dissolved in a halogenated solvent such as dichloromethane. The slow addition of hexanes precipitates the desired composition which is filtered and dried. In another embodiment of the present invention the desired phosphoramidite compositions are obtained by special request from a commercial source. Although these compositions are not available for sale from the general catalogs of commercial sources, a number of commercial sources were able to supply precipitated phosphoramidites on special request.

To be useful in the present invention, the phosphoramidite composition must closely mimic a highly purified phosphoramidite compound with regard to coupling efficiency. Stated another way, the overall yield and purity must be comparable to that obtained when using the highly purified phosphoramidite compound. To determine whether a phosphoramidite composition from a given source, e.g., in-house or other, is effective, the composition is first analyzed by HPLC to determine if the composition has particularly reactive side products present and, if so, what their concentration is. Dinucleoside side products, which can add to a growing chain and cause branching that is especially undesirable in more than about 0.2%, were synthesized and spiked into HPLC runs to help in the identification. Some processes of synthesis of phosphoramidites do not result in high concentrations of the types of side products that would diminish coupling efficiency and hence overall yield. Another test that was performed on a number of sources of phosphoramidite compositions was to simply prepare a 20-mer oligonucleotide. Each source of phosphoramidite compositions was used to prepare a 20-mer phosphorothioate oligonucleotide and compared to a standard phosphorothioate oligonucleotide prepared using highly purified phosphoramidites. In this way each source was evaluated to determine whether the final oligonucleotide was comparable to a standard oligonucleotide.

In one embodiment of the present invention phosphoramidite compositions resulting from precipitation after synthesis of the respective phosphoramidite compound are employed in the synthesis of oligomers. The general process for synthesis of the phosphoramidite compositions is shown below:

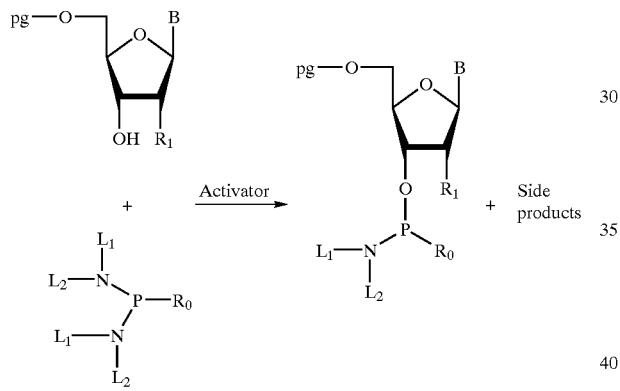

Relative to standard solid phase synthesis protocols for phosphoramidite chemistry, these side products or impurities can be classified as reactive or inert. Side products that are classified as inert may form further side products during the chain elongation step of oligomer synthesis, but this further side product is washed away during a subsequent rinse step as are other inert side products. Reactive side products are those that may negatively impact the oligomerization process by, for example, reducing the yield or purity of the desired product. Known inert side products formed during the preparation of 3'-phosphoramidites include nucleoside compounds having the formula:

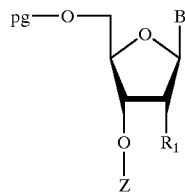

wherein Z is H or has one of the formulas:

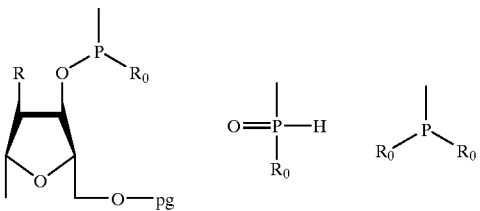

Known inert side products also include non-nucleosidic compounds having the formulas:

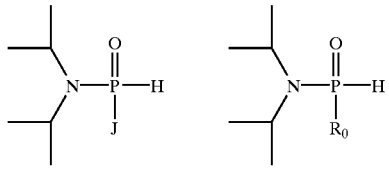

Reactive side products that will effect further chain elongation include those having the formula:

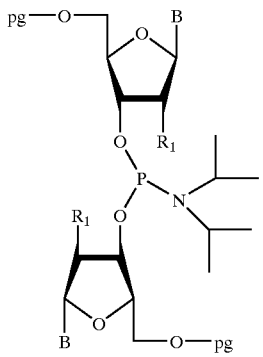

Reactive impurities having this formula are known to couple to the free hydroxyl group of an elongating chain and cause branching at the point of attachment from the two available 5'-positions upon further deblocking and chain elongation.

There are numerous processes known to the art skilled for the synthesis of phosphoramidite compounds. For example, the synthesis can involve a bis-amidite reagent or, alternatively, a halogenated amidite reagent. Additionally, processes may involve different solvents, temperatures, pH conditions or other experimental parameters. There are also undisclosed proprietary processes that are used to prepare phosphoramidites commercially. The particular process used to prepare phosphoramidite compounds determine the side products or impurities that may be present in the precipitated phosphoramidite composition. To be amenable to the present invention as a phosphoramidite composition substantially enriched in a phosphoramidite compound, the dried phosphoramidite composition, in addition to other criteria, must be about 99.8% free of reactive side products.

Prior to using a phosphoramidite composition of the present invention for routine oligomer synthesis, the phosphoramidite composition is evaluated to determine if it has less than about 0.2% of highly reactive side products. In one embodiment of the present invention, phosphoramidite compositions are analyzed by, for example, HPLC, NMR, $^{31}$P NMR, or mass spectroscopy to determine the presence of reactive side products. In another embodiment phosphoramidite compositions are used for the synthesis of oligomers and compared to the identical oligomer synthesized using phosphoramidites of high purity. In a preferred embodiment, phosphoramidite compositions of the present invention are assayed first and then used to synthesize oligomers for comparative analysis.

Phosphoramidites that were precipitated and dried but not purified further were obtained by special request from commercial sources. The phosphoramidites were assayed by HPLC to determine which impurities were present and what the overall purity was. In general, these precipitated phosphoramidites were greater than 92% pure. Spiking of samples with selected impurities, followed by comparison of the initial and spiked HPLC traces, allowed determination of the concentration of especially reactive side products. The phosphoramidite compositions, e.g., precipitated phosphoramidites containing side products, were used to prepare oligomers, and these compounds were compared to an identical oligomer. The comparison and the information obtained from the HPLC traces allowed the determination of allowable levels of particular impurities or side products, most notably reactive side products.

In one test, a uniform deoxyphosphorothioate 20-mer (SEQ ID NO: 1, TCC CGC CTG TGA CAT GCA TT) was prepared as a standard sequence using high purity phosphoramidites (from Pharmacia) for comparison to identical oligomers prepared using phosphoramidite compositions. The phosphoramidites for the standard sequence were assayed and were all equal to or above the industrial criteria discussed below, such as that the amidite is required to be greater than or equal to 99% pure and any single impurity is less than 0.5% as determined by HPLC.

Three additional batches identical to the standard sequence (SEQ ID NO: 1) were prepared using phosphoramidite compositions obtained from three separate sources. (See, Examples 5 and 14.) These compositions were obtained by special request and are not offered for sale in commercial catalogs. The phosphoramidite compositions contain precipitated phosphoramidite compounds made by the particular process used by the source supplying the composition. These phosphoramidites were assayed by HPLC and the results are shown below:

| Source | Base | % Purity (HPLC) |
|--------|------|-----------------|
| A | A | 96.7 |
| A | C | 95.7 |
| A | G | 92.8 |
| A | T | 97.8 |
| B | A | 94.3 |
| B | C | 95.5 |
| B | G | 92.8 |
| B | T | 97.2 |
| C | A, C, G, T | not assayed |

The standard sequence and each of the 3 batches were prepared following standard phosphoramidite methods and techniques for solid phase oligomerization. Purification of the resulting trityl on phosphorothioate oligomers was by standard reverse phase HPLC. All the trityl on fractions for each particular run were pooled for CGE and SAX analysis, which results are shown below:

| Amidite Source | Crude Yield OD/µmole | % Full Length Crude/Purified/(n − 1) | SAX P = S:P = 0 |
|----------------|---------------------|--------------------------------------|------------------|
| Pharmacia | 125 | 72.1/94.5 (1.7) | 99.5:0.5 |
| A | 127 | 72.5/94.6 (1.9) | 99.4:0.6 |
| B | 122 | 68.6/91.6 (3.7) | 99.4:0.6 |
| C | 110 | 66.9/94.0 (2.2) | 99.5:0.5 |

The phosphorothioate 20-mers prepared using the phosphoramidite compositions from sources A and B gave unexpectedly comparable results relative to the standard sequence prepared from high quality phosphoramidites.

After analysis of the comparative results of various oligomers prepared using both high purity phosphoramidites and phosphoramidite compositions, some preliminary criteria were formulated pertaining to phosphoramidite compositions amenable to the present invention. In a preferred embodiment the HPLC profile of a phosphoramidite composition gives the sum of the diastereoisomers to be greater than or equal to 92%. The HPLC is also performed with added standard amidite to verify that no shoulder or other peaks are present upon co-elution. This number is preliminary and could be lower dependent on the side products present in a given composition. Water and ethyl acetate content, as determined by GC, are preferably less than or equal to about 0.5% w/w and 3% w/w, respectively. The mole % of the phosphoramidite peak (148–150 native amidites) is greater than or equal to about 90% as determined by $^{31}P$ NMR. It should be noted that compositions of the present invention may, and often do, have other phosphorus species present in sharp contrast to high purity amidites.

Although there is no single set of criteria that is applied across the board in the industry with respect to the quality of phosphoramidites being used for the synthesis of oligomers, current criteria are very stringent. For example, one such criteria that is currently being used to evaluate phosphoramidites for use in the synthesis of oligomers intended as pharmaceuticals requires that the HPLC profile of a phosphoramidite give a relative retention ($\alpha$) of the sample and of a standard of from 0.95 to 1.05. The phosphoramidite is required to be greater than or equal to 99% pure and any single impurity is less than 0.5% by HPLC. It is preferred that the water and ethyl acetate content, as determined by GC, be less than or equal to about 0.5% w/w and 3% w/w, respectively. It is further preferred that the mole % of the phosphoramidite peak (148–150 native amidites) be greater than or equal to about 99% as determined by $^{31}P$ NMR. The sum of non-phosphoramidite peaks at 120 to 150 ppm should be less than or equal to 0.3%, and no other peaks above 170 ppm should be present, as determined by the $^{31}P$ NMR.

Phosphoramidite compositions, obtained by special request from commercial sources that sell high purity phosphoramidites, were assayed by HPLC to determine the purity and the major side products/contaminants present. The precipitated and dried deoxycyanoethoxy phosphoramidite compositions from one source gave the following data:

| Amidite | % Purity | % reactive side products |
|---|---|---|
| Guanosine | 95.5288 | |
| Cytidine | 97.2945 | |
| Adenosine | 97.2608 | |
| Thymidine | 97.6720 | 0.2063 |

In preferred embodiments, the methods of the present invention are employed in iterative solid phase oligonucleotide synthetic regimes. These methods are equally applicable to using modified nucleotides alone or in combination with native nucleotides to prepare non-naturally-occurring oligomers. Representative solid phase techniques are those typically employed for DNA and RNA synthesis utilizing standard phosphoramidite chemistry. See, e.g., Protocols For Oligonucleotides And Analogs, Agrawal, S., ed., Humana Press, Totowa, N.J., 1993, hereby incorporated by reference in its entirety. A preferred synthetic solid phase synthesis utilizes only phosphoramidites as activated phosphate compounds. In this technique, a phosphoramidite monomer is reacted with a free hydroxyl on the growing oligomer chain to produce an intermediate phosphite compound, which is subsequently oxidized to the $P^V$ state using standard methods. This technique is commonly used for the synthesis of several types of linkages including phosphodiester, phosphorothioate, and phosphorodithioate linkages.

Typically, the first step in such a process is attachment of a first monomer or higher order subunit containing a protected 5'-hydroxyl to a solid support, usually through a linker via the 3'- or the 2'-position, using standard methods and procedures known in the art. See, e.g., *Oligonucleotides And Analogues A Practical Approach*, Eckstein, F. Ed., IRL Press, N.Y., 1991, hereby incorporated by reference in its entirety. Solid supports are also commercially available having a first monomer subunit attached (Glen Research, Sterling, Va.). The support-bound monomer or higher order first synthon is then treated to remove the 5'-hydroxyl protecting group. Typically, this is accomplished by treatment with an acidic solution. The solid support bound monomer or higher order compound is then reacted with a phosphoramidite compound to form a compound having a phosphite or thiophosphite linkage. In preferred embodiments the coupling step is performed under anhydrous conditions in the presence of an activating agent such as, for example, 1H-tetrazole, 5-(4-nitrophenyl)-1H-tetrazole, or diisopropylamino tetrazolide.

It is generally preferable to perform a capping step, either prior to or after oxidation or sulfurization of the phosphite triester, thiophosphite triester, or dithiophosphite triester. Such a capping step is generally known to be beneficial by preventing shortened oligomer chains, by blocking chains that have not reacted in the coupling cycle. One representative reagent used for capping is acetic anhydride. Other suitable capping reagents and methodologies can be found in U.S. Pat. No. 4,816,571, issued Mar. 28, 1989, hereby incorporated by reference in its entirety.

Further treatment with an acid removes the 5'-hydroxyl protecting group, and thus transforms the solid support bound oligomer into a further reactive compound that can participate in the next synthetic iteration by reaction with a further phosphoramidite. This process is repeated until an oligomer of desired length is produced.

The resulting oligomer is protected at the 5'-end with, preferably, an acid labile protecting group, protected at reactive sites located on heterocyclic base moieties, such as exocyclic amino functionalities, with protecting groups protected at phosphorus by one or more phosphorus protecting groups, and is attached to a solid support by one of the 2'- or 3'-hydroxyl groups via a linker group such as a succinyl group. Deprotection and cleavage of the resultant oligomer is preferably by treatment with a reagent that allows deprotection of the base labile heterocyclic protecting groups and the phosphorus protecting groups first. This strategy allows for the removal of the compounds resulting from deprotection by standard rinsing of the solid support bound oligomer. Further treatment with a base under more vigorous conditions such as a solution having a higher pH or increased temperature or increasing the time of exposure will effect cleavage of the oligomer from the solid support. Treatment of the 5'-hydroxyl protecting group with an acidic solution at any time before or after general deprotection or cleavage yields the free 5'-hydroxyl group.

In a preferred deprotection/cleavage scheme the solid support bound, fully protected oligomer is first treated with a basic reagent effective to remove phosphorus and heterocyclic base protection. Such reagents can selectively remove the phosphorus and heterocyclic base protection without cleavage of the oligomer from the solid support. Representative reagents for this selective deprotection without simultaneous cleavage include, but are not limited to, DBU and triethylamine in ethanol.

The oligomer is next treated with a reagent effective to cleave the covalent linkage to the solid support. A preferred reagent for this cleavage is aqueous ammonia. Removal of the 5'-hydroxyl protecting group can be effected prior to or after purification by treatment with an acid solution. One advantage of purifying the oligomer with the protecting group present is that it aids in the purification process. The elution of the oligomer is slowed down, thus allowing impurities to be eluted first when doing HPLC purification using, for example, a $C_{18}$ reverse phase column.

In preferred embodiments, the methods of the invention are used for the preparation of oligomers including oligonucleotides and oligonucleotide analogs. The term "oligonucleotide" refers to a plurality of nucleotides joined together in a specific sequence from naturally and non-naturally occurring heterocyclic base moieties. As used herein, the term "oligonucleotide analog" means compounds that can contain both naturally-occurring (i.e., "natural") and non-naturally-occurring (i.e., "synthetic") moieties, such as nucleosidic subunits containing modified sugar and/or nucleobase portions. Such oligonucleotide analogs are typically structurally distinguishable from, yet functionally interchangeable with, naturally-occurring or synthetic wild-type oligonucleotides. Thus, oligonucleotide analogs include all such structures which function effectively to mimic the structure and/or function of a desired RNA or DNA strand, for example, by hybridizing to a target.

In the context of the present invention, the term "synthetic nucleoside" refers to a modified nucleoside. Representative modifications include modification of a heterocyclic base portion of a nucleoside to give a non-naturally-occurring nucleobase, a sugar portion of a nucleo-side, or both simultaneously.

In the context of this invention, a "heterocyclic ring system" is a cyclic compound containing at least one heteroatom such as N, O, or S. A "mixed heterocycle" is a cyclic compound containing at least two heteroatoms such as N, O or S. A "heteroaryl" compound is a heterocycle containing at least one heteroatom such as N, O or S and is not fully saturated, e.g., is in a state of partial or complete saturation. "Heteroaryl" is also meant to include fused systems including systems where one or more of the fused rings contain no heteroatoms.

Preferred heterocycles amenable to the present invention include, but are not limited to, imidazole, pyrrole, pyrazole, indole, 1H-indazole, α-carboline, carbazole, phenothiazine, phenoxazine, tetrazole, triazole, pyrrolidine, piperidine, piperazine and morpholine. A more preferred group of nitrogen heterocycles includes imidazole, pyrrole and carbazole.

Representative heterocyclic base moieties useful in the compounds and methods described herein include adenine, guanine, cytosine, uridine, and thymine, as well as other non-naturally-occurring and natural nucleobases such as xanthine, hypoxanthine, 2-aminoadenine, 6-methyl and other alkyl derivatives of adenine and guanine, 2-propyl and other alkyl derivatives of adenine and guanine, 5-halo uracil and cytosine, 6-azo uracil, cytosine and thymine, 5-uracil (pseudo uracil), 4-thiouracil, 8-halo, oxa, amino, thiol, thioalkyl, hydroxyl and other 8-substituted adenines and guanines, 5-trifluoromethyl and other 5-substituted uracils and cytosines, 7-methylguanine.

Preferred heterocyclic base moieties include adenine, $N^6$-benzoyladenine, cytosine, $N^4$-benzoylcytosine, 5-methylcytosine, $N^4$-benzoyl-5-methylcytosine, thymine, uracil, guanine, $N^2$-isobutyrylguanine, and 2-aminoadenine.

Further naturally- and non-naturally-occurring heterocyclic base moieties include those disclosed in U.S. Pat. No. 3,687,808 (Merigan, et al.), in chapter 15 by Sanghvi, in *Antisense Research and Application*, Ed. S. T. Crooke and B. Lebleu, CRC Press, 1993, in Englisch et al., *Angewandte Chemie*, International Edition, 1991, 30, 613–722 (see, especially pages 622 and 623, and in the *Concise Encyclopedia of Polymer Science and Engineering*, J. I. Kroschwitz Ed., John Wiley & Sons, 1990, pages 858–859, Cook, P. D., *Anti-Cancer Drug Design*, 1991, 6, 585–607, each of which is hereby incorporated by reference in its entirety. The term "heterocyclic base moiety" is further intended to include heterocyclic ring systems that can serve as nucleosidic bases including certain 'universal bases' that are not nucleosidic bases in the most classical sense but serve as nucleosidic bases. Especially mentioned as a universal base is 3-nitropyrrole.

As used herein, the term "phosphorus protecting group" refers to a group that is initially bound to the phosphorus atom of a phosphoramidite. The phosphorus protecting group functions to protect the phosphorus containing internucleotide linkage or linkages during, for example, solid phase oligonucleotide synthetic regimes. Treatment of the internucleotide linkage or linkages that have a phosphorus protecting group thereon with a deprotecting agent, such as aqueous ammonium hydroxide, will result in the removal of the phosphorus protecting group and leave a hydroxyl or thiol group in its place.

There are many phosphorus protecting groups known in the art which are useful in the present invention including, but not limited to, β-cyanoethyl, diphenylsilylethyl, δ-cyanobutenyl, cyano p-xylyl (CPX), methyl-N-trifluoroacetyl ethyl (META) and acetoxy phenoxy ethyl (APOE) groups. Phosphorus protecting groups are further described in Beaucage, S. L. and Iyer, R. P., Tetrahedron, 1993, 49, 1925–1963; Beaucage, S. L. and Iyer, R. P., *Tetrahedron*, 1993, 49, 10441–10488; and Beaucage, S. L. and Iyer, R. P., *Tetrahedron*, 1992, 48, 2223–2311. Representative United States patents that teach the preparation of phosphorus protecting groups and their incorporation into phosphoramidite compounds include, but are not limited to, U.S. Pat. Nos. 5,783,690; 5,760,209; 5,705621; 5,614,621; 5,453,496; 5,153,319; 5,132,418; 4,973,679; 4,725,677; 4,668,777; 4,500,707; 4,458,066; 4,415,732; and Re. 34,069, the entire contents of each of which are herein incorporated by reference.

Functional groups including those located on heterocyclic base moieties and 2'-sugar substituent groups are routinely blocked with protecting (blocking groups) during synthesis and subsequently deblocked. In general, a blocking group renders a chemical functionality of a molecule inert to specific reaction conditions and can later be removed from such functionality in a molecule without substantially damaging the remainder of the molecule. See, Green and Wuts, Protective Groups in Organic Synthesis, 2d edition, John Wiley & Sons, New York, 1991. For example, amino groups can be blocked with phthalimido, 9-fluorenyl-methoxycarbonyl (FMOC), triphenylmethylsulfenyl, t-BOC or benzyl groups. Carboxyl groups can be protected as acetyl groups. Representative hydroxyl protecting groups are described by Beaucage et al., *Tetrahedron* 1992, 48, 2223. Preferred hydroxyl protecting groups are acid-labile groups, such as the trityl, monomethoxytrityl, dimethoxytrityl, trimethoxytrityl, 9-phenylxanthine-9-yl (Pixyl) and 9-(p-methoxyphenyl)xanthine-9-yl (MOX). Chemical functional groups can also be "blocked" by including them in a precursor form. Thus an azido group can be considered a "blocked" form of an amine as the azido group is easily converted to the amine. Further representative protecting groups utilized in oligonucleotide synthesis are discussed in Agrawal et al., Protocols for Oligonucleotide Conjugates, Eds., Humana Press, New Jersey, 1994, Vol. 26, pp. 1–72.

As used herein, the term "oligonucleoside" includes oligomers or polymers containing two or more nucleoside subunits having a non-phosphorous linking moiety. Oligonucleosides according to the invention have a ribofuranose moiety attached to a nucleobase through a glycosyl bond. An oligonucleotide/nucleoside for the purposes of the present invention is a mixed backbone oligomer having at least two nucleosides covalently bound by a non-phosphate linkage and at least one phosphorous containing covalent bond with a nucleotide, wherein at least one of the monomeric nucleotide or nucleoside units is a 2'-O-substituted compound prepared using the process of the present invention. An oligonucleotide/nucleoside can additionally have a plurality of nucleotides and nucleosides coupled through phosphorous containing and/or non-phosphorous containing linkages.

As used herein, the term "sugar substituent group" or "2'-substituent group" includes groups attached to the 2'-position of the ribofuranosyl moiety with or without an oxygen atom. Sugar substituent groups amenable to the present invention include, but are not limited to, fluoro, O-alkyl, O-alkylamino, O-alkylalkoxy, protected O-alkylamino, O-alkylaminoalkyl, O-alkyl imidazole and polyethers of the formula $(O\text{-alkyl})_m$, wherein m is 1 to about 10. Preferred among these polyethers are linear and cyclic polyethylene glycols (PEGs), and (PEG)-containing groups, such as crown ethers and those which are disclosed by Ouchi et al., *Drug Design and Discovery* 1992, 9, 93; Ravasio et al., *J. Org. Chem.* 1991, 56, 4329; and Delgardo et. al., *Critical Reviews in Therapeutic Drug Carrier Systems* 1992, 9, 249, each of which is hereby incorporated by reference in its entirety. Further sugar modifications are disclosed in Cook, P. D., *Anti-Cancer Drug Design*, 1991, 6, 585–607. Fluoro, O-alkyl, O-alkylamino, O-alkyl imidazole, O-alkylaminoalkyl, and alkyl amino substitution is described in U.S. patent application Ser. No. 08/398,901, filed Mar. 6, 1995, entitled "Oligomeric Compounds having Pyrimidine Nucleotide(s) with 2' and 5' Substitutions," hereby incorporated by reference in its entirety.

Additional sugar substituent groups amenable to the present invention include 2'-SR and 2'-NR$_2$ groups, wherein each R is, independently, hydrogen, a protecting group or substituted or unsubstituted alkyl, alkenyl, or alkynyl. 2'-SR nucleosides are disclosed in U.S. Pat. No. 5,670,633, issued Sep. 23, 1997, hereby incorporated by reference in its entirety. The incorporation of 2'-SR monomer synthons is disclosed by Hamm et al., *J. Org. Chem.*, 1997, 62, 3415–3420. 2'-NR$_2$ nucleosides are disclosed by Goettingen, M., *J. Org. Chem.*, 1996, 61, 6273–6281; and Polushin et al., *Tetrahedron Lett.*, 1996, 37, 3227–3230. Further representative sugar substituent groups amenable to the present invention include those having one of formula I or II:

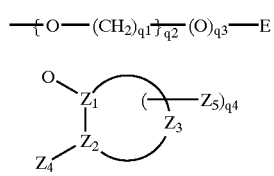

Representative 2'-O-sugar substituent groups of formula I are disclosed in U.S. patent application Ser. No. 09/130,973, filed Aug. 7, 1998, entitled "Capped 2'-Oxyethoxy Oligonucleotides," hereby incorporated by reference in its entirety.

Representative cyclic 2'-O-sugar substituent groups of formula II are disclosed in U.S. patent application Ser. No. 09/123,108, filed Jul. 27, 1998, entitled "RNA Targeted 2'-Modified Oligonucleotides that are Conformationally Preorganized," hereby incorporated by reference in its entirety.

Sugars having O-substitutions on the ribosyl ring are also amenable to the present invention. Representative substitutions for ring O include, but are not limited to, S, CH$_2$, CHF, and CF$_2$. See, e.g., Secrist et al., *Abstract 21, Program & Abstracts, Tenth International Roundtable, Nucleosides, Nucleotides and their Biological Applications*, Park City, Utah, Sep. 16–20, 1992, hereby incorporated by reference in its entirety.

Additional modifications may also be made at other positions on the oligonucleotide, particularly the 3' position of the sugar on the 3' terminal nucleotide and the 5'-position of 5' terminal nucleotide. For example, one additional modification of the oligonucleotides of the present invention involves chemically linking to the oligonucleotide one or more moieties or conjugates which enhance the activity, cellular distribution or cellular uptake of the oligonucleotide. Such moieties include, but are not limited to, lipid moieties such as a cholesterol moiety (Letsinger et al., *Proc. Natl. Acad. Sci. USA*, 1989, 86, 6553), cholic acid (Manoharan et al., *Bioorg. Med. Chem. Lett.*, 1994, 4, 1053), a thioether, e.g., hexyl-S-tritylthiol (Manoharan et al., *Ann. N.Y. Acad. Sci.*, 1992, 660, 306; Manoharan et al., *Bioorg. Med. Chem. Let.*, 1993, 3, ° 2765), a thiocholesterol (Oberhauser et al., *Nucl. Acids Res.*, 1992, 20, 533), an aliphatic chain, e.g., dodecandiol or undecyl residues (Saison-Behmoaras et al., *EMBO J.*, 1991, 10, 111; Kabanov et al., *FEBS Lett.*, 1990, 259, 327; Svinarchuk et al., *Biochimie*, 1993, 75, 49), a phospholipid, e.g., di-hexadecyl-rac-glycerol or triethylammonium-1,2-di-O-hexadecyl-rac-glycero-3-H-phosphonate (Manoharan et al., *Tetrahedron Lett.*, 1995, 36, 3651; Shea et al., *Nucl. Acids Res.*, 1990, 18, 3777), a polyamine or a polyethylene glycol chain (Manoharan et al., *Nucleosides & Nucleotides*, 1995, 14, 969), adamantane acetic acid (Manoharan et al., *Tetrahedron Lett.*, 1995, 36, 3651), a palmityl moiety (Mishra et al., *Biochim. Biophys. Acta*, 1995, 1264, 229), or an octadecylamine or hexylamino-carbonyl-oxycholesterol moiety (Crooke et al., *J. Pharmacol. Exp. Ther.*, 1996, 277, 923).

As used herein, the term "phosphorus protecting group" refers to a group that is initially bound to the phosphorus atom of a phosphoramidite. The phosphorus protecting group functions to protect the phosphorus containing internucleotide linkage or linkages during, for example, solid phase oligonucleotide synthetic regimes. Treatment of the internucleotide linkage or linkages that have a phosphorus protecting group thereon with a deprotecting agent such as aqueous ammonium hydroxide will result in the removal of the phosphorus protecting group and leave a hydroxyl or thiol group in its place.

There are many phosphorus protecting groups known in the art which are useful in the present invention including, but not limited, to β-cyanoethyl, diphenylsilylethyl, δ-cyanobutenyl, cyano p-xylyl (CPX), methyl-N-trifluoroacetyl ethyl (META), acetoxy phenoxy ethyl (APE) and butene-4-yl groups. Phosphorus protecting groups are further described in: Beaucage, S. L. and Iyer, R. P., *Tetrahedron*, 1993, 49, 1925–1963; Beaucage, S. L. and Iyer, R. P., *Tetrahedron*, 1993, 49, 10441–10488; Beaucage, S. L. and Iyer, R. P., *Tetrahedron*, 1992, 48, 2223–2311. Representative United States patents that teach the preparation of phosphorus protecting groups and their incorporation into phosphoramidite compounds include, but are not limited to, U.S. Pat. Nos. 5,783,690; 5,760,209; 5,705621; 5,614,621; 5,453,496; 5,153,319; 5,132,418; 4,973,679; 4,725,677; 4,668,777; 4,500,707; 4,458,066; 4,415,732; and Re. 34,069, the entire contents of each of which are herein incorporated by reference.

As used herein, the term "alkyl" includes, but is not limited to, straight chain, branched chain and alicyclic hydrocarbon groups. Alkyl groups of the present invention may be substituted. Representative alkyl substituents are disclosed in U.S. Pat. No. 5,212,295, at column 12, lines 41–50, hereby incorporated by reference in its entirety. As used herein, the term "lower alkyl" is intended to mean an alkyl group having 6 or fewer carbons.

As used herein, the term "aralkyl" denotes alkyl groups which bear aryl groups, for example, benzyl groups. The term "alkaryl" denotes aryl groups which bear alkyl groups, for example, methylphenyl groups. As used herein, the term "aryl" denotes aromatic cyclic groups including, but not limited to, phenyl, naphthyl, anthracyl, phenanthryl and pyrenyl.

As used herein, the term "alkanoyl" has its accustomed meaning as a group of formula —C(=O)-alkyl. A preferred alkanoyl group is the acetyl group.

In general, the term "hetero" denotes an atom other than carbon, preferably, but not exclusively, N, O, or S. Accordingly, the term "heterocycloalkyl" denotes an alkyl ring system having one or more heteroatoms (i.e., non-carbon atoms). Preferred heterocycloalkyl groups include, for example, morpholino groups. As used herein, the term "heterocycloalkenyl" denotes a ring system having one or more double bonds and one or more heteroatoms. Preferred heterocycloalkenyl groups include, for example, pyrrolidino groups.

In some preferred embodiments of the present invention, a first nucleoside or oligomer is attached to a solid support using an optional linker. Solid supports are substrates which are capable of serving as the solid phase in solid phase synthetic methodologies, such as those described in U.S.

Pat. Nos. 4,415,732; 4,458,066; 4,500,707; 4,668,777; 4,973,679; and 5,132,418 (Caruthers); and U.S. Pat. Nos. 4,725,677 and Re. 34,069 (Koster). Linkers are known in the art as short molecules which serve to connect a solid support to functional groups (e.g., hydroxyl groups) of initial synthon molecules in solid phase synthetic techniques. Suitable linkers are disclosed in, for example, *Oligonucleotides And Analogues A Practical Approach*, Eckstein, F. Ed., IRL Press, N.Y., 1991, Chapter 1, pages 1–23.

Solid supports according to the present invention include those generally known in the art to be suitable for use in solid phase methodologies, including, for example, controlled pore glass (CPG), oxalyl-controlled pore glass. See, e.g., Alul et al., *Nucleic Acids Research* 1991, 19, 1527, hereby incorporated by reference in its entirety. Solid supports further include TentaGel Support, which is an aminopolyethyleneglycol derivatized support (Wright et al., *Tetrahedron Letters* 1993, 34, 3373, hereby incorporated by reference in its entirety) and Poros, which is a copolymer of polystyrene/divinylbenzene.

Hydroxyl protecting groups according to the present invention include a wide variety of groups. Preferably, the protecting group is stable under basic conditions but can be removed under acidic conditions. In general, protecting groups render chemical functionalities inert to specific reaction conditions, and can be appended to and removed from such functionalities in a molecule without substantially damaging the remainder of the molecule. Representative hydroxyl protecting groups are disclosed by Beaucage et al., *Tetrahedron* 1992, 48, 2223–2311, and Greene and Wuts, *Protective Groups in Organic Synthesis*, Chapter 2, 2d ed, John Wiley & Sons, New York, 1991, each of which is hereby incorporated by reference in its entirety. Preferred protecting groups used for $R_2$, $R_3$ and $R_{3a}$ include, but are not limited to, dimethoxytrityl (DMT), monomethoxytrityl, 9-phenylxanthen-9-yl (Pixyl) and 9-(p-methoxyphenyl)xanthen-9-yl (Mox). The $R_2$ or $R_3$ group can be removed from oligomers of the invention by techniques well known in the art to form the free hydroxyl. For example, dimethoxytrityl protecting groups can be removed by protic acids such as formic acid, dichloroacetic acid, trichloroacetic acid, p-toluene sulphonic acid or with Lewis acids such as for example zinc bromide. See, e.g., Greene and Wuts, supra.

In some preferred embodiments of the present invention, amino groups are appended to alkyl or to other groups such as, for example, 2'-alkoxy groups. Such amino groups are also commonly present in naturally-occurring and non-naturally-occurring nucleobases. It is generally preferred that these amino groups be in protected form during the synthesis of oligomers of the invention. Representative amino protecting groups suitable for these purposes are discussed in Greene and Wuts, *Protective Groups in Organic Synthesis*, Chapter 7, 2d ed, John Wiley & Sons, New York, 1991. Generally, as used herein, the term "protected," when used in connection with a molecular moiety such as "nucleobase," indicates that the molecular moiety contains one or more functionalities protected by protecting groups.

Sulfurizing agents used during oxidation to form phosphorothioate and phosphorodithioate linkages include Beaucage reagent (Iyer, R. P. et.al., *J. Chem. Soc.*, 1990, 112, 1253–1254, and Iyer, R. P. et.al., *J. Org. Chem.*, 1990, 55, 4693–4699); tetraethylthiuram disulfide (Vu, H., Hirschbein, B.L., *Tetrahedron Lett.*, 1991, 32, 3005–3008); dibenzoyl tetrasulfide (Rao, M. V. et.al., *Tetrahedron Lett.*, 1992, 33, 4839–4842); di(phenylacetyl)disulfide (Kamer, P. C. J., Tetrahedron Lett., 1989, 30, 6757–6760); bis(O,O-diisopropoxy phosphinothioyl)disulfides (Stec et al., *Tetrahedron Lett.*, 1993, 34, 5317–5320); 3-ethoxy-1,2,4-dithiazoline-5-one (*Nucleic Acids Research*, 1996 24, 1602–1607, and *Nucleic Acids Research*, 1996 24, 3643–3644); bis(p-chlorobenzenesulfonyl)disulfide (*Nucleic Acids Research*, 1995 23, 4029–4033); sulfur, sulfur in combination with ligands like triaryl, trialkyl, triaralkyl, or trialkaryl phosphines. The foregoing references are hereby incorporated by reference in their entirety.

Useful oxidizing agents used to form the phosphodiester or phosphorothioate linkages include iodine/tetrahydrofuran/water/pyridine or hydrogen peroxide/water or tert-butyl hydroperoxide or any peracid like m-chloroperbenzoic acid. In the case of sulfurization, the reaction is performed under anhydrous conditions with the exclusion of air, in particular oxygen, whereas in the case of oxidation the reaction can be performed under aqueous conditions.

Oligonucleotides or oligonucleotide analogs according to the present invention hybridizable to a specific target preferably comprise from about 5 to about 50 monomer subunits. It is more preferred that such compounds comprise from about 10 to about 30 monomer subunits, with 15 to 25 monomer subunits being particularly preferred. When used as "building blocks" in assembling larger oligomers, smaller oligomers are preferred.

In one aspect of the present invention, compounds of the invention are used to modulate RNA or DNA, which code for a protein whose formation or activity it is desired to modulate. The targeting portion of the composition to be employed is, thus, selected to be complementary to the preselected portion of DNA or RNA that is to be hybridizable to that portion.

In the compounds and methods of the present invention, $X_1$ and $X_2$ are, independently, O or S. Thus, compounds having chiral phosphorus linkages are contemplated by the present invention. See, Stec, W. J. and Lesnikowski, Z. J., in *Methods in Molecular Biology* Vol. 20: *Protocols for Oligonucleotides and Analogs*, S. Agrawal, Ed., Humana Press, Totowa, N.J. (1993), at Chapter 14. See, also Stec, W. J. et al., *Nucleic Acids Research*, Vol. 19, No. 21, 5883–5888 (1991); and European Patent Application EP 0 506 242 A1, each of which is hereby incorporated by reference in its entirety.

The oligomers of the present invention can be used in diagnostics, therapeutics and as research reagents and kits. They can be used in pharmaceutical compositions by including a suitable pharmaceutically acceptable diluent or carrier. They further can be used for treating organisms having a disease characterized by the undesired production of a protein. The organism is contacted with an oligonucleotide having a sequence that is capable of specifically hybridizing with a strand of nucleic acid coding for the undesirable protein. Treatment of this type can be practiced on a variety of organisms ranging from unicellular prokaryotic and eukaryotic organisms to multicellular eukaryotic organisms. Any organism that utilizes DNA-RNA transcription or RNA-protein translation as a fundamental part of its hereditary, metabolic or cellular control is susceptible to therapeutic and/or prophylactic treatment in accordance with the present invention. Seemingly diverse organisms, such as bacteria, yeast, protozoa, algae, all plants and all higher animal forms, including warm-blooded animals, can be treated. Further, each cell of multicellular eukaryotes can be treated, as they include both DNA-RNA transcription and RNA-protein translation as integral parts of their cellular activity. Furthermore, many of the organelles (e.g., mitochondria and chloroplasts) of eukaryotic cells also include transcription and translation mechanisms. Thus, single cells, cellular populations or organelles can also be included within the definition of organisms that can be treated with therapeutic or diagnostic oligonucleotides.

The formulation of therapeutic compositions and their subsequent administration is believed to be within the skill of those in the art. In general, for therapeutics, a patient in need of such therapy is administered an oligomer in accordance with the invention, commonly in a pharmaceutically acceptable carrier, in doses ranging from 0.01 µg to 100 g per kg of body weight depending on the age of the patient and the severity of the disease state being treated. Further, the treatment may be a single dose or may be a regimen that may last for a period of time which will vary depending upon the nature of the particular disease, its severity and the overall condition of the patient, and may extend from once daily to once every 20 years. Following treatment, the patient is monitored for changes in his/her condition and for alleviation of the symptoms of the disease state. The dosage of the oligomer may either be increased in the event the patient does not respond significantly to current dosage levels, or the dose may be decreased if an alleviation of the symptoms of the disease state is observed, or if the disease state has been ablated.

In some cases it may be more effective to treat a patient with an oligomer of the invention in conjunction with ther traditional therapeutic modalities. For example, a patient being treated for AIDS may be administered an oligomer in conjunction with AZT, or a patient with atherosclerosis may be treated with an oligomer of the invention following angioplasty to prevent reocclusion of the treated arteries.

Dosing is dependent on severity and responsiveness of the disease condition to be treated, with the course of treatment lasting from several days to several months, or until a cure is effected or a diminution of disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligomers, and can generally be estimated based on $EC_{50}$s found to be effective in in vitro and in vivo animal models. In general, dosage is from 0.01 µg to 100 g per kg of body weight, and may be given once or more daily, weekly, monthly or yearly, or even once every 2 to several years.

Following successful treatment, it may be desirable to have the patient undergo maintenance therapy to prevent the recurrence of the disease state, wherein the oligomer is administered in maintenance doses, ranging from 0.01 µg to 100 g per kg of body weight, once or more daily, to once every several years.

The pharmaceutical compositions of the present invention may be administered in a number of ways depending upon whether local or systemic treatment is desired and upon the area to be treated. Administration may be topical (including ophthalmic, vaginal, rectal, intranasal, transdermal), oral or parenteral. Parenteral administration includes intravenous drip, subcutaneous, intraperitoneal or intramuscular injection, or intrathecal or intraventricular administration.

Formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

Compositions for oral administration include powders or granules, suspensions or solutions in water or non-aqueous media, capsules, sachets or tablets. Thickeners, flavoring agents, diluents, emulsifiers, dispersing aids or binders may be desirable.

Compositions for intrathecal or intraventricular administration may include sterile aqueous solutions which may also contain buffers, diluents and other suitable additives.

Formulations for parenteral administration may include sterile aqueous solutions which may also contain buffers, diluents and other suitable additives.

As will be recognized, the steps of the methods of the present invention need not be performed any particular number of times or in any particular sequence. Additional objects, advantages, and novel features of this invention will become apparent to those skilled in the art upon examination of the following illustrative examples, which are not intended to be limiting.

EXAMPLES

Example 1

Synthesis of T-T Phosphorothioate Dimer

5'-O-dimethoxytritylthymidine (100 mg, 4 mmole) bonded to CPG (controlled pore glass) through an ester linkage was taken in a glass reactor and a dichloromethane solution of 2% dichloroacetic acid (volume/volume) was added to deprotect the 5'-hydroxyl group. The product was washed with dichloromethane and then with acetonitrile. Then, a 0.2 M solution of 5'-O-(4,4'-dimethoxytrityl) thymidine-3'-O-(2-cyanoethyl)-N,N-diisopropyl phosphoramidite (obtained as a composition) in acetonitrile and a 0.45 M solution of 1H-tetrazole in acetonitrile was added, and reacted at room temperature for 5 minutes. The product was washed with acetonitrile, and then a 0.05 M solution of Beaucage reagent in acetonitrile was added and reacted at room temperature for 5 minutes. This sulfurization step was repeated one more time for 5 minutes. The support was washed with acetonitrile and then a solution of acetic anhydride/lutidine/THF (1:1:8), and N-methyl imidazole/ THF was added to cap the unreacted 5'-hydroxyl group. The product was washed with acetonitrile.

The solid support was treated with aqueous 30% ammonium hydroxide for 90 minutes. The aqueous solution was filtered, concentrated under reduced pressure to give the title T-T dimer.

Example 2

Synthesis of C-T Phosphorothioate Dimer

5'-O-dimethoxytritylthymidine (100 mg, 4 mmole) bonded to CPG (controlled pore glass) through an ester linkage was taken in a glass reactor, and a dichloromethane solution of 2% dichloroacetic acid (volume/volume) was added to deprotect the 5'-hydroxyl group. The product was washed with acetonitrile. Then, a 0.2 M solution of $N^4$-Benzoyl-5'-O-(4,4'-dimethoxytrityl)-2'-deoxycytidine-3'-O-(2-cyanoethyl)-N,N-diisopropyl phosphoramidite (obtained as a composition) in acetonitrile and a 0.4 M solution of 1H-tetrazole in acetonitrile was added, and reacted at room temperature for 5 minutes. The product was washed with acetonitrile, and then a 0.05 M solution of Beaucage reagent in acetonitrile was added and reacted at room temperature for 5 minutes. This sulfurization step was repeated one more time for 5 minutes. The support was washed with acetonitrile and then a solution of acetic anhydride/lutidine/THF (1:1:8), and N-methyl imidazole/ THF was added to cap the unreacted 5'-hydroxyl group. The product was washed with acetonitrile.

The solid support was treated with aqueous 30% ammonium hydroxide for 90 minutes followed by incubation at 55° C. for 12 hours. The resulting mixture was filtered and the resulting solution was filtered, concentrated under reduced pressure and treated at room temperature with 1.0 M solution of tetra-n-butyl ammonium fluoride in THF to give the title phosphorothioate dC-T dimer.

Example 3

Synthesis of 5'-TTTTTTT-3' Phosphorothioate Heptamer

5'-O-dimethoxytritylthymidine (50 mg, 2 mmole) bound to CPG (controlled pore glass) through an ester linkage was taken up in a glass reactor, and a toluene solution of 3% dichloroacetic acid (volume/volume) was added to deprotect the 5'-hydroxyl group. The product was washed with acetonitrile. Then, a 0.2 M solution of 5'-Q-(4,4'-dimethoxytrityl) thymidine-3'-O-(2-cyanoethyl)-N,N-diisopropyl phosphoramidite (obtained as a composition) in acetonitrile and a 0.4 M solution of 1H-tetrazole in acetonitrile was added, and allowed to react at room temperature for 5 minutes. The product was washed with acetonitrile, and then a 0.2 M solution of phenylacetyl disulfide in acetonitrile:3-picoline (1:1 v/v) was added and allowed to react at room temperature for 3 minutes. This sulfurization step was repeated one more time for 3 minutes. The support was washed with acetonitrile, and then a solution of acetic anhydride/lutidine/THF (1:1:8), and N-methyl imidazole/THF was added to cap any unreacted 5'-hydroxyl group. The product was washed with acetonitrile.

This complete cycle was repeated five more times to produce the completely protected thymidine heptamer. The carrier containing the compound was treated with 30% aqueous ammonium hydroxide solution for 90 minutes at room temperature. The aqueous solution was filtered, and concentrated under reduced pressure to give a phosphorothioate heptamer, TTTTTTT.

Example 4

Synthesis of 5'-d(GACT)-3' Phosphorothioate Tetramer

5'-O-dimethoxytritylthymidine (50 mg, 2 mmole) bound to CPG (controlled pore glass) through an ester linkage was taken up in a glass reactor, and a toluene solution of 3% dichloroacetic acid in toluene (volume/volume) was added to deprotect the 5'-hydroxyl group. The product was washed with acetonitrile. Then, a 0.2 M solution of 5'-O-(4,4'-dimethoxytrityl)thymidine-3'-O-(2-cyanoethyl)-N,N-diisopropyl phosphoramidite (obtained as a composition) in acetonitrile and a 0.4 M solution of 1H-tetrazole in acetonitrile was added, and allowed to react at room temperature for 5 minutes. The product was washed with acetonitrile, and then a 0.2 M solution of phenylacetyl disulfide in acetonitrile:3-picoline (1:1 v/v) was added and allowed to react at room temperature for 3 minutes. This sulfurization step was repeated one more time for 3 minutes. The support was washed with acetonitrile and then a solution of acetic anhydride/lutidine/THF (1:1:8), and N-methyl imidazole/THF was added to cap the unreacted 5'-hydroxyl group. The product was washed with acetonitrile.

A solution of 3% dichloroacetic acid in toluene (volume/volume) was added to deprotect the 5'-hydroxyl group. The product was washed with acetonitrile. Then, a 0.2 M solution of $N^4$-benzoyl-$5^1$-O-(4,4'-dimethoxytrityl)-2'-deoxycytidine-3'-O-(2-cyanoethyl)-N,N-diisopropyl phosphoramidite (obtained as a composition) in acetonitrile and a 0.4 M solution of 1H-tetrazole in acetonitrile was added, and allowed to react at room temperature for 5 minutes. The product was washed with acetonitrile, and then a 0.2 M solution of phenylacetyl disulfide in acetonitrile:3-picoline (1:1 v/v) was added and allowed to react at room temperature for 3 minutes. This sulfurization step was repeated one more time for 3 minutes. The support was washed with acetonitrile and then a solution of acetic anhydride/lutidine/THF (1:1:8), and N-methyl imidazole/THF was added to cap any unreacted 5'-hydroxyl group. The product was washed with acetonitrile.

A solution of 3% dichloroacetic acid in toluene (volume/volume) was added to deprotect the 5'-hydroxyl group. The product was washed with acetonitrile. Then, a 0.2 M solution of $N^6$-benzoyl-5'-O-(4,4'-dimethoxytrityl)-2'-deoxyadenosine-3'-O-(2-cyanoethyl)-N,N-diisopropyl phosphoramidite (obtained as a composition) in anhydrous acetonitrile and a 0.4 M solution of 1H-tetrazole in acetonitrile was added, and allowed to react at room temperature for 5 minutes. The product was washed with acetonitrile, and then a 0.2 M solution of phenylacetyl disulfide in acetonitrile:3-picoline (1:1 v/v) was added and allowed to react at room temperature for 3 minutes. This sulfurization step was repeated one more time for 3 minutes. The support was washed with acetonitrile and then a solution of acetic anhydride/lutidine/THF (1:1:8), and N-methyl imidazole/THF was added to cap the unreacted 5'-hydroxyl group. The product was washed with acetonitrile.

A solution of 3% dichloroacetic acid in toluene (volume/volume) was added to deprotect the 5'-hydroxyl group. The product was washed with acetonitrile. Then, a 0.2 M solution of therapeutic grade $N^2$-isobutyryl-5'-O-(4,4'-dimethoxytrityl)-2'-deoxyguanosine-3'-O-(2-cyanoethyl)-N,N-diisopropyl phosphoramidite (obtained as a composition) in acetonitrile and a 0.4 M solution of 1H-tetrazole in acetonitrile was added, and allowed to react at room temperature for 5 minutes. The product was washed with acetonitrile, and then a 0.2 M solution of phenylacetyl disulfide in acetonitrile:3-picoline (1:1 v/v) was added and allowed to react at room temperature for 3 minutes. This sulfurization step was repeated one more time for 3 minutes. The support was washed with acetonitrile and then a solution of acetic anhydride/lutidine/THF (1:1:8), and N-methyl imidazole/THF was added to cap any unreacted 5'-hydroxyl group. The product was washed with acetonitrile.

The carrier containing the compound was treated with 30% aqueous ammonium hydroxide solution for 90 minutes at room temperature and then incubated at 55° C. for 24 hour. The aqueous solution was filtered, concentrated under reduced pressure to give a phosphorothioate tetramer of 5'-dG-dA-dC-T-3'.

Example 5

Synthesis of Fully-modified 5'-d(TCC-CGC-CTG-TGA-CAT-GCA-TT)-3' Phosphorothioate 20-mer (SEQ ID NO: 1)

The synthesis of the above sequence was performed on a Pharmacia OligoPilot II Synthesizer on a 180 mmole scale using the cyanoethyl phosphoramidites obtained from Pharmacia as compositions and Pharmacia's HL 30 primar support. Detritylation was performed using 3% dichloroacetic acid in toluene (volume/volume). Phosphoramidites were activated with a 0.4 M solution of 1H-tetrazole in acetonitrile. Sulfurization was performed using a 0.2 M solution of phenylacetyl disulfide in acetonitrile:3-picoline (1:1 v/v) for 2 minutes. At the end of synthesis, the support was washed with acetonitrile, cleaved, deprotected and purified in the usual manner.

Example 6

Synthesis of Fully-modified 5'-d(GCC-CAA-GCT-GGC-ATC-CGT-CA)-3' Phosphorothioate 20-mer (SEQ ID NO: 2)

The synthesis of the above sequence was performed on a Pharmacia OligoPilot II Synthesizer on a 180 mmole scale using the cyanoethyl phosphoramidites obtained from Pharmacia as the compositions and Pharmacia's HL 30 primar support. Detritylation was performed using 3% dichloroacetic acid in toluene (volume/volume). Phosphoramidites were activated with a 0.4 M solution of 1H-tetrazole in acetonitrile. Sulfurization was performed using a 0.2 M solution of phenylacetyl disulfide in acetonitrile:3-picoline (1:1 v/v) for 2 minutes. At the end of synthesis, the support was washed with acetonitrile, cleaved, deprotected and purified in the usual manner.

Example 7

Synthesis of Fully-modified 5'-d(GCG-TTT-GCT-CTT-CTT-CTT-GCG)-3' Phosphorothioate 21-mer (SEQ ID NO: 3)

The synthesis of the above sequence was performed on a Pharmacia OligoPilot II Synthesizer on a 180 mmole scale using the corresponding cyanoethyl phosphoramidites as compositions and Pharmacia's primar support. Detritylation was performed using 3% dichloroacetic acid in toluene (volume/volume). Phosphoramidites were activated with a 0.4 M solution of 1H-tetrazole in acetonitrile. Sulfurization was performed using a 0.2 M solution of phenylacetyl disulfide in acetonitrile:3-picoline (1:1 v/v) for 2 minutes. At the end of synthesis, the support was washed with acetonitrile, cleaved, deprotected and purified in the usual manner.

Example 8

Synthesis of Fully-modified 5'-d(GTT-CTC-GCT-GGT-GAG-TTT-CA)-3' Phosphorothioate 20-mer (SEQ ID NO: 4)

The synthesis of the above sequence was performed on a Pharmacia OligoPilot II Synthesizer on a 180 mmole scale using the cyanoethyl phosphoramidites as the compositions and Pharmacia's HL 30 primar support. Detritylation was performed using 3% dichloroacetic acid in toluene (volume/volume). Phosphoramidites were activated with a 0.4 M solution of 1H-tetrazole in acetonitrile. Sulfurization was performed using a 0.2 M solution of phenylacetyl disulfide in acetonitrile:3-picoline (1:1 v/v) for 2 minutes. At the end of synthesis, the support was washed with acetonitrile, cleaved, deprotected and purified in the usual manner.

Example 9

Synthesis of Fully-modified 5'-d(TCC-GTC-ATC-GCT-CCT-CAG-GG)-3' Phosphorothioate 20-mer (SEQ ID NO: 5)

The synthesis of the above sequence was performed on a Pharmacia OligoPilot II Synthesizer on a 180 mmole scale using the cyanoethyl phosphoramidites obtained as the compositions from Pharmacia and Pharmacials HL 30 primar support. Detritylation was performed using 3% dichloroacetic acid in toluene (volume/volume). Phosphoramidites were activated with a 0.4 M solution of 1H-tetrazole in acetonitrile. Sulfurization was performed using a 0.2 M solution of phenylacetyl disulfide in acetonitrile:3-picoline (1:1 v/v) for 2 minutes. At the end of synthesis, the support was washed with acetonitrile, cleaved, deprotected and purified in the usual manner.

Example 10

Synthesis of Fully-modified 5'-d(TCC-GTC-ATC-GCT-CCT-CAG-GG)-3' Phosphorothioate 20-mer (SEQ ID NO: 5)

The synthesis of the above sequence was performed on a Pharmacia OligoPilot II Synthesizer on a 180 mmole scale using the cyanoethyl phosphoramidites obtained from Cruachem Inc., Aston, Pa., as the compositions and Pharmacia's HL 30 primar support. Detritylation was performed using 3% dichloroacetic acid in toluene (volume/volume). Phosphoramidites were activated with a 0.4 M solution of 1H-tetrazole in acetonitrile. Sulfurization was performed using a 0.2 M solution of phenylacetyl disulfide in acetonitrile:3-picoline (1:1 v/v) for 2 minutes. At the end of synthesis, the support was washed with acetonitrile, cleaved, deprotected and purified in the usual manner.

Example 11

Synthesis of Fully-modified 5'-d(TCC-GTC-ATC-GCT-CCT-CAG-GG)-3' Phosphorothioate 20-mer (SEQ ID NO: 5)

The synthesis of the above sequence was performed on a Pharmacia OligoPilot II Synthesizer on a 180 mmole scale using the cyanoethyl phosphoramidites obtained from Proligo LLC, Boulder, Colo., as the compositions and Pharmacia's HL 30 primar support. Detritylation was performed using 3% dichloroacetic acid in toluene (volume/volume). Phosphoramidites were activated with a 0.4 M solution of 1H-tetrazole in acetonitrile. Sulfurization was performed using a 0.2 M solution of phenylacetyl disulfide in acetonitrile:3-picoline (1:1 v/v) for 2 minutes. At the end of synthesis, the support was washed with acetonitrile, cleaved, deprotected and purified in the usual manner.

Example 12

Synthesis of Fully-modified 5'-d(GCC-CAA-GCT-GGC-ATC-CGT-CA)-3' Phosphorothioate 20-mer (SEQ ID NO: 2)

The synthesis of the above sequence was performed on a Pharmacia OligoPilot II Synthesizer on a 180 mmole scale using the cyanoethyl phosphoramidites obtained from Cruachem Inc., Aston, Pa., as the compositions, and Pharmacia's HL 30 primar support. Detritylation was performed using 3% dichloroacetic acid in toluene (volume/volume). Phosphoramidites were activated with a 0.4 M solution of 1H-tetrazole in acetonitrile. Sulfurization was performed using a 0.2 M solution of phenylacetyl disulfide in acetonitrile:3-picoline (1:1 v/v) for 2 minutes. At the end of synthesis, the support was washed with acetonitrile, cleaved, deprotected and purified in the usual manner.

Example 13

Synthesis of Fully-modified 5'-d(GCC-CAA-GCT-GGC-ATC-CGT-CA)-3' Phosphorothioate 20-mer (SEQ ID NO: 2)

The synthesis of the above sequence was performed on a Pharmacia OligoPilot II Synthesizer on a 180 mmole scale using the cyanoethyl phosphoramidites obtained from Proligo LLC, Boulder, Colo., as the compositions and Pharmacia's HL 30 primar support. Detritylation was performed using 3% dichloroacetic acid in toluene (volume/volume). Phosphoramidites were activated with a 0.4 M solution of 1H-tetrazole in acetonitrile. Sulfurization was performed using a 0.2 M solution of phenylacetyl disulfide in acetonitrile:3-picoline (1:1 v/v) for 2 minutes. At the end of synthesis, the support was washed with acetonitrile, cleaved, deprotected and purified in the usual manner.

Example 14

General Procedure for the Synthesis of Deoxy P=S 20-mer (5'-TCC CGC CTG TGA CAT GCA TT) (SEQ ID NO: 1)

The synthesis of the above sequence was performed on a Pharmacia OligoPilot II Synthesizer on a 180 mmole scale using the cyanoethyl phosphoramidites as the respective compositions that were obtained by special request from commercial sources that sell high purity phosphoramidites. Pharmacials HL 30 thymidine primar support was used. Detritylation was performed using 3% dichloroacetic acid in toluene (volume/volume). Phosphoramidites were activated with a 0.4 M solution of 1H-tetrazole in acetonitrile. Sulfurization was performed using a 0.2 N solution of phenylacetyl disulfide in acetonitrile:3-picoline (1:1 v/v) for 2 minutes. At the end of synthesis, the support was washed with acetonitrile, cleaved, deprotected and purified in the usual manner. The oligonucleotide was purified by reversed phase HPLC and all DMT fractions were combined and analyzed by capillary gel electrophoresis.

It is intended that each of the patents, applications, printed publications, and other published documents mentioned or referred to in this specification be herein incorporated by reference in their entirety.

Those skilled in the art will appreciate that numerous changes and modifications may be made to the preferred embodiments of the invention and that such changes and modifications may be made without departing from the spirit of the invention. It is therefore intended, that the appended claims cover all such equivalent variations as fall within the true spirit and scope of the invention.

What is claimed is:

1. A method of preparing an oligomer having at least one moiety of formula:

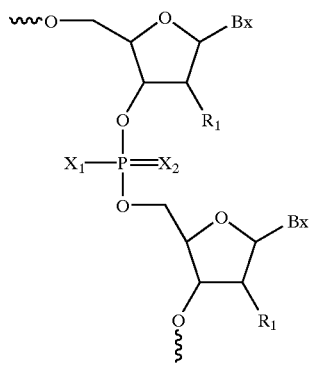

wherein:

each $X_1$ and $X_2$ is, independently, O or S;

Bx is a protected or unpprotected heterocyclic base moiety; and each $R_1$ is, independently, H, a protected hydroxyl group, a sugar substituent group or a protected sugar substituent group;

comprising the steps of:

providing a compound of the formula:

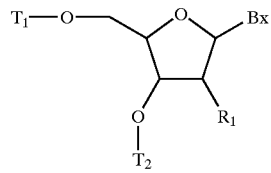

wherein:

$T_1$ is a hydroxyl protecting group; and $T_2$ is a covalent attachment to a solid support or a solid support bound nucleoside, nucleotide, oligonucleoside or oligonucleotide;

removing the $T_1$ group to form said compound having a 5'-hydroxyl group; and treating said compound having a 5'-hydroxyl group with a phosphoramidite composition to form an extended compound, said phosphoramidite composition comprising a phosphoramidite compound of the formula:

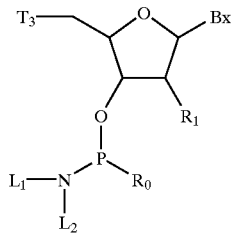

wherein:

$T_3$ is a protected hydroxyl group, a nucleoside, a nucleotide, an oligonucleoside or an oligonucleotide;

$R_0$ is a phosphorus protecting group; and each $L_1$ and $L_2$ is, independently, $C_{1-4}$ alkyl;

or $L_1$ and $L_2$ are joined together to form a 4 to 7-membered heterocyclic ring system including the nitrogen atom to which $L_1$ and $L_2$ are attached, wherein said ring system optionally includes at least one additional heteroatom selected from O, N and S;

said phosphoramidite composition Her comprising at least about 2% by weight of impurities comprising at least one 3'-hydroxy nucleoside, a pill species different from said phosphoramidite compound where covalent attachment of groups to the $P^{III}$ phosphorus of said $P^{III}$ species is through oxygen or sulfur, or a $P^V$ species where covalent attachment of groups to the $P^V$ species is through oxygen, sulfur or nitrogen.

2. The method of claim 1 further comprising treating said extended compound with a capping agent to form a capped compound.

3. The method of claim 1 further comprising treating said capped compound with an oxidizing agent to form an oxidized compound.

4. The method of claim 3 further comprising treating said oxidized compound with a reagent effective to deprotect said oxidized compound to form a deprotected oligomer.

5. The method of claim 4 further comprising treating said deprotected oligomer with a reagent effective to cleave said oligomer from the solid support.

6. The method of claim 4 wherein said reagent is also effective to cleave the deprotected oligomer from the solid support.

7. The method of claim 1 further comprising treating said extended compound with a reagent effective to remove the protecting group from said protected hydroxyl group.

8. The method of claim 1 wherein said heterocyclic base moiety is adenine, $N^6$-benzoyladenine, cytosine, N$^4$-benzoylcytosine, 5-methylcytosine, N$^4$-benzoyl-5-methyl-cytosine, thymine, uracil, guanine, N$^2$-isobutyrylguanine or 2-aminoadenine.

9. The method of claim 1 wherein each $L_1$ and $L_2$ is, independently, $C_{16}$ alkyl.

10. The method of claim 9 wherein each $L_1$ and $L_2$ is, independently, isopropyl.

11. The method of claim 1 wherein $L_1$ and $L_2$ are joined together to form a heterocyclic ring system including the nitrogen atom to which said $L_1$ and $L_2$ are attached, wherein said ring system optionally includes at least one additional heteroatom selected from O, N and S.

12. The method of claim 11 wherein said heterocyclic ring system is morpholine.

13. The method of claim 1 wherein each $R_1$, is, independently, H, hydroxyl, $C_1$–$C_{20}$ alkyl, $C_3$–$C_{20}$ alkenyl, $C_2$–$C_{20}$ alkynyl, halogen, thiol, keto, carboxyl, nitro, nitroso, nitrile, trifluoromethyl, trifluoromethoxy, O-alkyl, S-alkyl, NH-alkyl, N-dialkyl, O-aryl, S-aryl, NH-aryl, O-aralkyl, S-aralkyl, NH-aralkyl, amino, N-phthalimido, imidazole, azido, hydrazino, hydroxylamino, isocyanato, sulfoxide, sulfone, sulfide, disulfide, silyl, aryl, heterocycle, carbocycle, intercalator, reporter molecule, conjugate, polyamine, polyamide, polyalkylene glycol or polyether;

or $R_1$ has one of formula I or II:

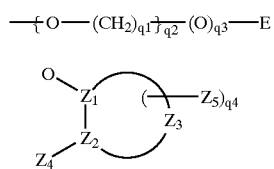

wherein:
E is $C_1$–$C_{10}$ alkyl, $N(Q_1)(Q_2)$ or $N=C(Q_1)(Q_2)$;
each $Q_1$ and $Q_2$ is, independently, H, $C_1$–$C_{10}$ alkyl, dialkylaminoalkyl, a nitrogen protecting group, a tethered or untethered conjugate group, a linker to a solid support;
or $Q_1$ and $Q_2$, together, form a nitrogen protecting group or a ring structure optionally including at least one additional heteroatom selected from N and O;
$q^1$ is an integer from 1 to 10;
$q^2$ is an integer from 1 to 10;
$q^3$ is 0 or 1;
$q^4$ is, 0, 1 or 2;
$Z_4$ is $OM_1$, $SM_1$, or $N(M_1)_2$;
each $M_1$ is, independently, H, $C_1$–$C_8$ alkyl, $C_1$–$C_8$ haloalkyl, $C(=NH)N(H)M_2$, $C(=O)N(H)M_2$ or $OC(=O)N(H)M_2$;
$M_2$ is H or $C_1$–$C_8$ alkyl;
each $Z_1$, $Z_2$ and $Z_3$ is, independently, $C_4$–$C_7$ cycloalkyl, $C_5$–$C_{14}$ aryl or $C_3$–$C_{15}$ heterocyclyl, wherein the heteroatom in said heterocyclyl group is selected from oxygen, nitrogen and sulfur; and
$Z_5$ is $C_1$–$C_{10}$ alkyl, $C_1$–$C_{10}$ haloalkyl, $C_2$–$C_{10}$ alkenyl, $C_2$–$C_{10}$ alkynyl, $C_6$–$C_{14}$ aryl, $N(Q_1)(Q_2)$, $OQ_1$, halo, $SQ_1$ or CN.

14. The method of claim 1 wherein said phosphorus protecting group is $X_3$—J, wherein $X_3$ is O or S and J is $CH_2CH_2CN$, diphenylsilylethyl, δ-cyanobutenyl, cyano p-xylyl (CPX), methyl-N-trifluoroacetyl ethyl (META) or acetoxy phenoxy ethyl (APOE).

15. The method of claim 1 wherein said phosphoramidite composition comprises at least about 98% by weight of said phosphoramidite compound.

16. The method of claim 1 wherein said phosphoramidite composition comprises at least about 97% by weight of said phosphoramidite compound.

17. The method of claim 1 wherein said phosphoramidite composition comprises at least about 95% by weight of said phosphoramidite compound.

18. The method of claim 1 wherein said phosphoramidite composition comprises at least about 90% by weight of said phosphoramidite compound.

19. The method of claim 1 wherein said phosphoramidite composition comprises at least about 80% by weight of said phosphoramidite compound.

20. The method of claim 1 wherein said phosphoramidite composition comprises at least about 75% by weight of said phosphoramidite compound.

21. The method of claim 1 wherein each of said $X_1$ and $X_2$ are O.

22. The method of claim 1 wherein each of said $X_1$ and $X_2$ are S.

23. The method of claim 1 wherein one of said $X_1$ and $X_2$ is O and the other of said $X_1$ and $X_2$ is S.

24. The method of claim 1 wherein said compound having a 5'-hydroxyl group is treated with said phosphoramidite composition in the presence of an activating agent.

25. The method of claim 24 wherein said activating agent is 1-H-tetrazole.

26. A method of linking a nucleotide to a further nucleotide, nucleoside, oligonucleoside or oligonucleotide having a 5'-hydroxyl group thereon comprising treating said further nucleotide, nucleoside, oligonucleoside or oligonucleotide having a 5'-hydroxyl group with a phosphoramidite composition to form an extended compound, said phosphoramidite composition comprising a phosphoramidite compound of the formula:

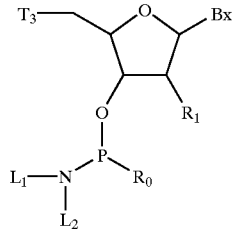

wherein:
$T_3$ is a protected hydroxyl group, a nucleoside, a nucleotide, an oligonucleoside or an oligonucleotide;
Bx is a protected or unprotected heterocyclic base moiety;
each $R_1$ is, independently, H, a protected hydroxyl group, a sugar substituent group or a protected sugar substituent group;
$R_0$ is a phosphorus protecting group; and
each $L_1$ and $L_2$ is, independently, $C_{1-6}$ alkyl;
or $L_1$ and $L_2$ are joined together to form a 4- to 7-membered heterocyclic ring system including the nitrogen atom to which $L_1$ and $L_2$ are attached, wherein said ring system optionally includes at least one additional heteroatom selected from O, N and S;
said phosphoramidite composition further comprising at least about 2% by weight of impurities comprising at least one 3'-hydroxy nucleoside, a $P^{III}$ species different from said phosphoramidite compound where covalent attachment of groups to the $P^{III}$ phosphorus of said $P^{III}$ species is through oxygen or sulfur, or a $P^V$ species where covalent attachment of groups to the $P^V$ species is by oxygen, sulfur or nitrogen.

27. The method of claim 26 further comprising treating said extended compound with a capping agent to form a capped compound.

28. The method of claim 27 further comprising treating said capped compound with an oxidizing agent to form an oxidized compound.

29. The method of claim 28 further comprising treating said oxidized compound with a reagent effective to deprotect said oxidized compound to form a deprotected oligomer.

30. The method of claim 29 further comprising treating said deprotected oligomer with a reagent effective to cleave said oligomer from the solid support.

31. The method of claim 26 further comprising treating said extended compound with a reagent effective to remove the protecting group from said protected hydroxyl group.

32. The method of claim 26 wherein said phosphoramidite composition comprises at least about 98% by weight of said phosphoramidite compound.

33. The method of claim 26 wherein said phosphoramidite composition comprises at least about 97% by weight of said phosphoramidite compound.

34. The method of claim 26 wherein said phosphoramidite composition comprises at least about 95% by weight of said phosphoramidite compound.

35. The method of claim 26 wherein said phosphoramidite composition comprises at least about 90% by weight of said phosphoramidite compound.

36. The method of claim 26 wherein said phosphoramidite composition comprises at least about 80% by weight of said phosphoramidite compound.

37. The method of claim 26 wherein said phosphoramidite composition comprises at least about 75% by weight of said phosphoramidite compound.

38. A method of preparing an oligomer having at least one moiety of formula:

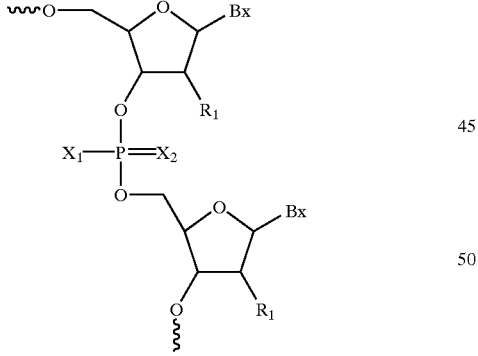

wherein:

each $X_1$ and $X_2$ is, independently O or S;

$B_x$ is a protected or unprotected heterocyclic base moiety; and each $R_1$ is, independently, H, a protected hydroxyl group, a sugar substituent group or a protected sugar substituent group;

comprising the steps of:
providing a compound of the formula:

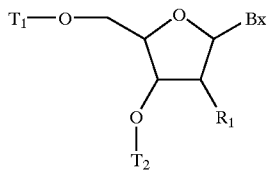

wherein:

$T_1$ is a hydroxyl protecting group; and $T_2$ is a covalent attachment to a solid support or a solid support bound nucleoside, nucleotide, oligonucleoside or oligonucleotide;

removing the $T_1$ group to form said compound having a 5'-hydroxyl group; and treating said compound having a 5'-hydroxyl group with a phosphoramidite composition to form an extended compound, said phosphoramidite composition comprising a phosphoramidite compound of the formula:

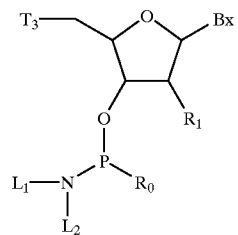

wherein:

$T_3$ is a protected hydroxyl group, a nucleoside, a nucleotide, an oligonucleoside or an oligonucleotide;

$R_0$ is a phosphorus protecting group; and each $L_1$ and $L_2$ is, independently, $C_{1-6}$ alkyl;

or $L_1$ and $L_2$ are joined together to form a 4 to 7-membered heterocyclic ring system including the nitrogen atom to which $L_1$ and $L_2$ are attached, wherein said ring system optionally includes at least one additional heteroatom selected from O, N and S;

said phosphoramidite composition further comprising at least about 1% by weight of impurities having one of the following formulas:

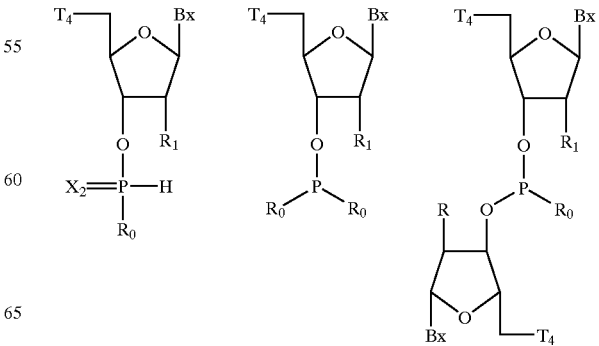

-continued

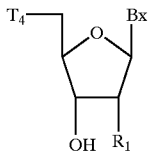 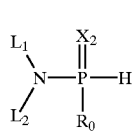 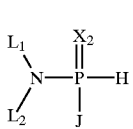

wherein:

each $X_2$ is, independently, O or S;

each J is $CH_2CH_2CN$, diphenylsilylethyl, δ-cyanobutenyl, cyano p-xylyl (CPX), methyl-N-trifluoroacetyl ethyl (META) or acetoxy phenoxy ethyl (APOE);

each $T_4$ is, independently, a hydroxyl group or a protected hydroxyl group;

each $R_0$ is a phosphorus protecting group;

each $L_1$ and $L_2$ is, independently, $C_{1-6}$ alkyl;

or $L_1$ and L2 are joined together with the nitrogen atom to which they are attached to form a 4- to 7-membered heterocyclic ring system, wherein said ring system optionally includes at least one additional heteroatom selected from O, N and S;

each $B_x$ is a protected or unprotected heterocyclic base moiety; and each $R_1$ is, independently, H, a protected hydroxyl group, a sugar substituent group or a protected sugar substituent group.

39. The method of claim 38 further comprising treating said extended compound with a capping agent to form a capped compound.

40. The method of claim 38 further comprising treating said capped compound with an oxidizing agent to form an oxidized compound.

41. The method of claim 40 further comprising treating said oxidized compound with a reagent effective to deprotect said oxidized compound to form a deprotected oligomer.

42. The method of claim 41 further comprising treating said deprotected oligomer with a reagent effective to cleave said oligomer from the solid support.

43. The method of claim 41 wherein said reagent is also effective to cleave the deprotected oligomer from the solid support.

44. The method of claim 38 further comprising treating said extended compound with a reagent effective to remove the protecting group from said protected hydroxyl group.

45. The method of claim 38 wherein said heterocyclic base moiety is adenine, $N^6$-benzoyladenine, cytosine, $N^4$-benzoylcytosine, 5-methylcytosine, $N^4$-benzoyl-5-methylcytosine, thymine, uracil, guanine, $N^2$-isobutyrylguanine or 2-aminoadenine.

46. The method of claim 38 wherein each $L_1$ and $L_2$ is, independently, $C_{1-6}$ alkyl.

47. The method of claim 46 wherein each $L_1$ and $L_2$ is, independently, isopropyl.

48. The method of claim 38 wherein $L_1$ and $L_2$ are joined together to form a heterocyclic ring system including the nitrogen atom to which said $L_1$ and $L_2$ are attached, wherein said ring system optionally includes at least one additional heteroatom selected from O, N and S.

49. The method of claim 48 wherein said heterocyclic ring system is morpholine.

50. The method of claim 38 wherein each $R_1$, is, independently, H, hydroxyl, $C_1$–$C_{20}$ alkyl, $C_3$–$C_{20}$ alkenyl, $C_2$–$C_{20}$ alkynyl, halogen, thiol, keto, carboxyl, nitro, nitroso, nitrile, trifluoromethyl, trifluoromethoxy, O-alkyl, S-alkyl, NH-alkyl, N dialkyl, O-aryl, S-aryl, $N^4$-aryl, O-aralkyl, S-aralkyl, NH-aralkyl, amino, N-phthalimido, imidazole, azido, hydrazino, hydroxylamino, isocyanato, sulfoxide, sulfone, sulfide, disulfide, silyl, aryl, heterocycle, carbocycle, intercalator, reporter molecule, conjugate, polyamine, polyamide, polyalkylene glycol or polyether;

or $R_1$ has one of formula I or II:

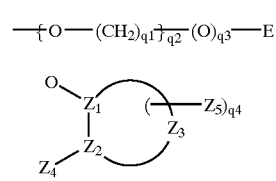

wherein:

E is $C_1$–$C_{10}$ alkyl, $N(Q_1)(Q_2)$ or $N=C(Q_1)(Q_2)$;

each $Q_1$ and Q2 is, independently, H, $C_1$–$C_{10}$ alkyl, dialkylaminoalkyl, a nitrogen protecting group, a tethered or untethered conjugate group, a linker to a solid support;

or $Q_1$ and Q2, together, form a nitrogen protecting group or a ring structure optionally including at least one additional heteroatom selected from N and O;

$q^1$ is an integer from 1 to 10;

$q^2$ is an integer from 1 to 10;

$q^3$ is 0 or 1;

$q^4$ is, 0, 1 or 2;

$Z_4$ is $OM_1$, $SM_1$, or $NM_1)_2$;

each $M_1$ is, independently, H, $C_1$–$C_8$ alkyl $C_1$–$C_8$ haloalkyl, $C(=NH)N(H))M_2$, $C(=O)N(H)M_2$ or $OC(=O)N(H)M_2$;

$M_1$ is H or $C_1$–$C_8$ alkyl;

each $Z_1$, $Z_2$ and $Z_3$ is, independently, $C_4$–$C_7$ cycloalkyl, $C_5$–$C_{14}$ aryl or $C_3$–$C_{15}$ heterocyclyl, wherein the heteroatom in said heterocyclyl group is selected from oxygen, nitrogen and sulfur; and $Z_5$ is $C_1$–$C_{10}$ alkyl, $C_1$–$C_{10}$ haloalkyl, $C_2$–$C_{10}$ alkenyl, $C_2$–$C_{10}$ alkynyl, $C_6$–$C_{14}$ aryl, $N(Q_1)(Q_2)$, $OQ_1$, halo, $SQ_1$ or CN.

51. The method of claim 38 wherein said phosphorus protecting group is $X_3$—J, wherein $X_3$ is O or S and J is $CH_2CH_2CN$, diphenylsilylethyl, 8-cyanobutenyl, cyano p-xylyl (CPX), methyl-N-trifluoroacetyl ethyl (META) or acetoxy phenoxy ethyl (APOE).

52. A method of preparing an oligomer having at least one moiety of formula:

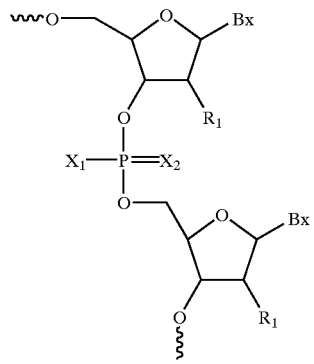

wherein:

each $X_1$ and $X_2$ is, independently, O or S;

Bx is a protected or unprotected heterocyclic base moiety; and each $R_1$ is, independently, H, a protected hydroxyl group, a sugar substituent group or a protected sugar substituent group, said method comprising the steps of:
(a) providing a phosphoramidite composition, said phosphoramidite composition comprising an amidite of formula:

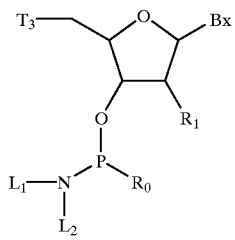

wherein:

$T_3$ is a protected hydroxyl group, a nucleoside, a nucleotide, an oligonucleoside or an oligonucleotide;

$R_0$ is a phosphorus protecting group; and each $L_1$ and $L_2$ is, independently, $C_{1-6}$ alkyl;

or $L_1$ and $L_2$ are joined together to form a 4 to 7-membered heterocyclic ring system including the nitrogen atom to which $L_1$ and $L_2$ are attached, wherein said ring system optionally includes at least one additional heteroatom selected from O, N and S, said phosphoramidite composition further comprising at least about 1% by weight of inert impurities, said impurities comprising at least one 3'-hydroxy nucleoside, a $P^{III}$ phosphorus species different from said phosphoramidite compound where covalent attachment of groups to the $P^{III}$ phosphorus of said $P^{III}$ species is through oxygen or sulfur, or a $P^V$ species where covalent attachment of groups to the $P^V$ species is through oxygen, sulfur or nitrogen;

(b) assaying the phosphoramidite composition, whereby said at least about 1% by weight of inert impurities are detected;

(c) providing a compound of formula:

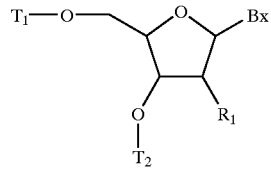

wherein $T_1$ is a hydroxyl protecting group; and $T_2$ is a covalent attachment to a solid support or a solid support bound nucleoside, nucleotide, oligonucleoside or oligonucleotide; and (d) reacting the compound of step (c) with the phosphoramidite composition of step (b) to form an extended compound.

53. The method of claim 38, wherein said inert impurities comprise at least one compound selected from:

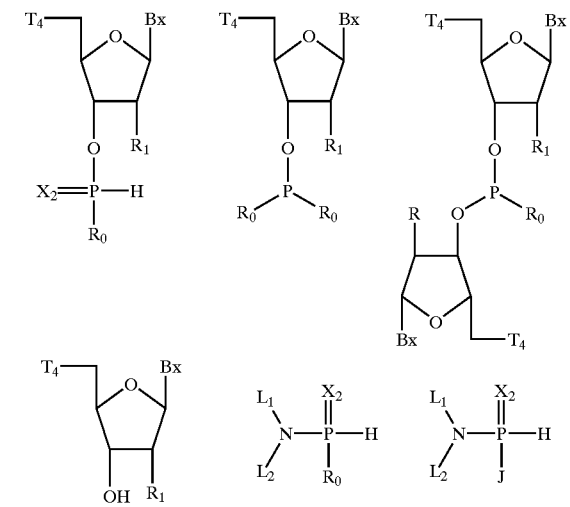

wherein:

each $X_2$ is, independently, O or S;

each J is $CH_2CH_2CN$, diphenylsilylethyl δ-cyanobutenyl, cyano p-xylyl (CPX), methyl-N-trifluoroacetyl ethyl (META) or acetoxy phenoxy ethyl (APOE);

each $T_4$ is, independently, a hydroxyl group or a protected hydroxyl group, each $R_0$ is a phosphorus protecting group;

each $L_1$ and $L_2$ is, independently, $C_{1-6}$ alkyl;

or $L_1$ and $L_2$ are joined together with the nitrogen atom to which they are attached to form a 4- to 7-membered heterocyclic ring system, wherein said ring system optionally includes at least one additional heteroatom selected from O, N and S;

each $B_x$ is a protected or unprotected heterocyclic base moiety; and each $R_1$ is, independently, H, a protected hydroxyl group, a sugar substituent group or a protected sugar substituent group.

54. The method of claim 52 wherein said phosphoramidite composition comprises at least about 2% by weight of inert impurities, said impurities comprising at least one 3'-hydroxy nucleoside, a $P^{III}$ phosphorus species different from said phosphoramidite compound where covalent attachment of groups to the $P^{III}$ phosphorus of said $P^{III}$ species is through oxygen or sulfur, or a $P^V$ species where covalent attachment of groups to the $P^V$ species is through oxygen, sulfur or nitrogen.

* * * * *

UNITED STATES PATENT AND TRADEMARK OFFICE
CERTIFICATE OF CORRECTION

PATENT NO.    : 6,610,842 B1  
DATED         : August 26, 2003  
INVENTOR(S)   : Ravikumar et al.

It is certified that error appears in the above-identified patent and that said Letters Patent is hereby corrected as shown below:

<u>Column 34,</u>
Line 39, delete the word "Her" and insert therefor -- further --.
Line 41, delete the word "pill" and insert therefor -- $p^{III}$ --.

Signed and Sealed this

Ninth Day of December, 2003

JAMES E. ROGAN
*Director of the United States Patent and Trademark Office*